(12) United States Patent
Anthony et al.

(10) Patent No.: US 7,332,499 B2
(45) Date of Patent: Feb. 19, 2008

(54) SULFONYL SUBSTITUTED N-(BIARYLMETHYL) AMINOCYCLOPROPANECARBOXAMIDES

(75) Inventors: Neville J. Anthony, Chalfont, PA (US); Robert Gomez, Perkasie, PA (US); Samson M. Jolly, Lansdale, PA (US); John Jin Lim, Perkiomenville, PA (US); Dai-shi Su, Dresher, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 10/565,040

(22) PCT Filed: Aug. 3, 2004

(86) PCT No.: PCT/US2004/025037

§ 371 (c)(1),
(2), (4) Date: Jan. 18, 2006

(87) PCT Pub. No.: WO2005/016886

PCT Pub. Date: Feb. 24, 2005

(65) Prior Publication Data

US 2006/0247229 A1    Nov. 2, 2006

Related U.S. Application Data

(60) Provisional application No. 60/493,257, filed on Aug. 7, 2003, provisional application No. 60/493,146, filed on Aug. 7, 2003.

(51) Int. Cl.
*A61K 31/505* (2006.01)
*A61K 31/12* (2006.01)
*C07D 417/00* (2006.01)
*C07D 239/00* (2006.01)
*C07C 233/00* (2006.01)

(52) U.S. Cl. .................. 514/269; 514/676; 544/55; 544/335; 564/123

(58) Field of Classification Search ................ 544/335, 544/55; 514/269, 676; 564/123
See application file for complete search history.

(56) References Cited

U.S. PATENT DOCUMENTS

| 5,182,288 | A | 1/1993 | Murray et al. |
| 6,919,343 | B2 * | 7/2005 | Wood et al. ................. 514/256 |
| 7,091,380 | B2 * | 8/2006 | Wood et al. ................. 564/155 |
| 7,163,951 | B2 * | 1/2007 | Kuduk et al. ............... 514/336 |
| 2005/0085667 | A1 | 4/2005 | Wood et al. |
| 2005/0288305 | A1 | 12/2005 | Kuduk et al. |

FOREIGN PATENT DOCUMENTS

CA    2050769    3/1992

* cited by examiner

*Primary Examiner*—Janet L. Andres
*Assistant Examiner*—Binta Robinson
(74) *Attorney, Agent, or Firm*—Mollie M. Yang; Valerie J. Camara

(57) ABSTRACT

N-(Sulfonyloxybiarylmethyl) aminocyclopropanecarboxamide derivatives are bradykinin B1 antagonists or inverse agonists useful in the treatment or prevention of symptoms such as pain and inflammation associated with the bradykinin B1 pathway.

11 Claims, No Drawings

SULFONYL SUBSTITUTED N-(BIARYLMETHYL) AMINOCYCLOPROPANECARBOXAMIDES

CROSS REFERENCE TO RELATED APPLICATIONS

This application is the National Stage of International Application No. PCT/US2004/025037, filed 3 Aug. 2004 which claims the benefit under 35 U.S.C. 119(e) of U.S. Provisional Application No. 60/493,146 filed 7 Aug. 2003 and U.S. Provisional Application No. 60/493,257 filed 7 Aug. 2003.

BACKGROUND OF THE INVENTION

This invention is directed to aminocyclopropanecarboxamide compounds. In particular, this invention is directed to aminocyclopropanecarboxamide compounds that are bradykinin antagonists or inverse agonists.

Bradykinin ("BK") is a kinin which plays an important role in the pathophysiological processes accompanying acute and chronic pain and inflammation. Bradykinin (BK), like other kinins, is an autacoid peptide produced by the catalytic action of kallikrein enzymes on plasma and tissue precursors termed kininogens. The biological actions of BK are mediated by at least two major G-protein-coupled BK receptors termed B1 and B2. It is generally believed that B2 receptors, but not B1 receptors, are expressed in normal tissues and that inflammation, tissue damage or bacterial infection can rapidly induce B1 receptor expression. This makes the B1 receptor a particularly attractive drug target. The putative role of kinins, and specifically BK, in the management of pain and inflammation has provided the impetus for developing potent and selective BK antagonists. In recent years, this effort has been heightened with the expectation that useful therapeutic agents with analgesic and anti-inflammatory properties would provide relief from maladies mediated through a BK receptor pathway (see e.g., M. G. Bock and J. Longmore, Current Opinion in Chem. Biol., 4:401-406 (2000)). Accordingly, there is a need for novel compounds that are effective in blocking or reversing activation of bradykinin receptors. Such compounds would be useful in the management of pain and inflammation, as well as in the treatment or prevention of diseases and disorders mediated by bradykinin; further, such compounds are also useful as research tools (in vivo and in vitro).

Canadian Published Application No. 2,050,769 discloses compounds of the formula:

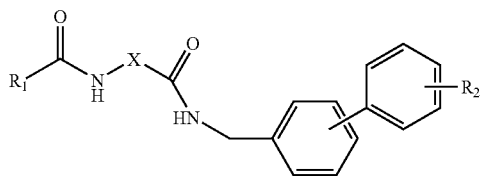

which are intermediates in the preparation of angiotensin II antagonists.

SUMMARY OF TE INVENTION

The present invention provides biphenyl cyclopropanecarboxamide derivatives which are bradykinin antagonists or inverse agonists, pharmaceutical compositions containing such compounds, and methods of using them as therapeutic agents.

DETAILED DESCRIPTION OF THE INVENTION

The present invention provides compounds of formula I and pharmaceutically acceptable salts thereof:

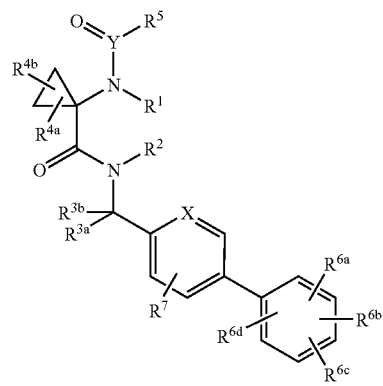

wherein
$R^1$ and $R^2$ are independently selected from hydrogen and $C_{1-4}$ allyl;
$R^{3a}$ and $R^{3b}$ are independently selected from hydrogen and $C_{1-4}$ alkyl optionally substituted with 1 to 5 halogen atoms;
$R^{4a}$ and $R^{4b}$ are independently selected form hydrogen, halogen, and $C_{1-4}$ alkyl optionally substituted with 1 to 4 groups selected from halogen, $OR^a$, $OC(O)R^a$, $S(O)_k R^d$, $OS(O)_2 R^d$, and $NR^1 R^2$, or
$R^{4a}$ and $R^{4b}$ together with the carbon atom to which they are both attached form an exo-cyclic methylene optionally substituted with 1 to 2 groups selected from $C_{1-4}$ alkyl optionally substituted with 1-5 halogens and $C_{1-4}$ alkyloxy;
$R^5$ is selected from (1) $C_{1-6}$ alkyl optionally substituted with 1 to 5 groups independently selected from halogen, nitro, cyano, $OR^a$, $SR^a$, $COR^a$, $SO_2 R^d$, $CO_2 R^a$, $OC(O)R^a$, $NR^b R^c$, $NR^b C(O)R^a$, $NR^b C(O)_2 R^a$, $C(O)NR^b R^c$, $C_{3-8}$ cycloalkyl, (2) $C_{3-8}$ cycloalkyl optionally substituted with 1 to 5 groups independently selected from halogen, nitro, cyano and phenyl, (3) $C_{3-6}$ alkynyl, (4) $C_{2-6}$ alkenyl optionally substituted with hydroxyethyl, (5) $(CH_2)_k$-aryl optionally substituted with 1 to 3 groups independently selected from halogen, nitro, cyano, $OR^a$, $SR^a$, $C(O)_2 R^a$, $C_{1-4}$ alkyl and $C_{1-3}$ haloalkyl; (6) $(CH_2)_k$-heterocycle optionally substituted with 1 to 3 groups independently selected from halogen, nitro, cyano, $OR^a$, $SR^a$, $C_{1-4}$ alkyl and $C_{1-3}$ haloalkyl wherein said heterocycle is selected from (a) a 5-membered heteroaromatic ring having a ring heteroatom selected from N, O and S, and optionally having up to 3 additional ring nitrogen atoms wherein said ring is optionally benzo-fused; (b) a 6-membered heteroaromatic ring containing from 1 to 3 ring nitrogen atoms and N-oxides thereof, wherein said ring is optionally benzo-fused; and (c) a 5- or 6-membered non-aromatic heterocyclic ring selected from tetrahydrofuranyl, 5-oxotetrahydrofuranyl, 2-oxo-2H-pyranyl, 6-oxo-1,6-dihydropyridazinyl, (7) $C(O)_2 R^a$, and (8) $C(O)NR^b R^c$;
$R^{6a}$ is selected from (1) $-OSO_2 R^8$, (2) $-NR^{8a} SO_2 R^9$, and (3) $-C(R^{8b})(R^{8c})SO_2 R^9$;
$R^{6b}$, $R^{6c}$, and $R^{6d}$ are independently selected from (1) hydrogen, (2) halogen, (3) $OSO_2 R^8$, (4) $C_{1-4}$ alkyl optionally substituted with 1 to 5 halogen atoms, (5) cyano, (6) nitro, (7) OR$^a$, and (8) CO$_2$R$^a$, or when attached to adjacent carbon atoms R$^{6c}$ and R$^{6d}$ together with the carbon atoms to which they are attached form a 5- to 8-membered saturated or unsaturated ring;

R$^7$ is selected from (1) hydrogen, (2) halogen, (3) cyano, (4) nitro, (5) OR$^a$, (6) CO$_2$R$^a$, (7) C(O)NR$^b$R$^c$, and (8) C$_{1-4}$ alkyl optionally substituted with 1 to 5 halogen atoms, R$^8$ is selected from (1) C$_{1-4}$ alkyl optionally substituted with 1 to 5 halogen atoms, (2) (CH$_2$)$_k$-aryl optionally substituted with 1 to 3 groups independently selected from halogen, nitro, cyano, NR$^a$C(O)R$^a$, OR$^a$, SR$^a$, CO$_2$R$^a$, C$_{1-4}$ alkyl, C$_{1-3}$ haloalkyl and NR$^b$R$^c$, (3) NR$^b$R$^c$, and (4) hydrogen;

R$^{8a}$ is selected from hydrogen, C$_{1-4}$ alkyl optionally substituted with 1 to 5 halogen atoms, halogen, and CO$_2$R$^a$, or when R$^{6a}$ and R$^{6b}$ are attached to adjacent atoms, R$^{8a}$ and R$^{6b}$ together complete 5- or 6-membered ring;

R$^{8b}$ and R$^{8c}$ are independently selected from hydrogen, C$_{1-4}$ alkyl optionally substituted with 1 to 5 halogen atoms, halogen, cyano, nitro, CO$_2$R$^a$, and OR$^a$;

R$^9$ is selected from (1) C$_{1-4}$ alkyl optionally substituted with 1 to 5 halogen atoms, (2) aryl optionally substituted with 1 to 3 groups independently selected from halogen, nitro, cyano, NR$^a$(C)OR$^a$, OR$^a$, SR$^a$, CO$_2$R$^a$, C$_{1-4}$ alkyl and C$_{1-3}$ haloalkyl, and (3) (CH$_2$)$_k$-aryl optionally substituted with 1 to 3 groups independently selected from halogen, nitro, cyano, NR$^a$(COR$^a$), OR$^a$, SR$^a$, CO$_2$R$^a$, C$_{1-4}$ alkyl and C$_{1-3}$ haloalkyl, or R$^{8a}$ and R$^9$ together with the atoms to which they are attached form a 5- to 8-membered heterocyclic ring;

R$^a$, R$^b$ and R$^c$ are independently selected from (1) hydrogen, (2) C$_{1-4}$ alkyl optionally substituted with 1 to 5 halogen atoms, (3) phenyl optionally substituted with 1 to 3 groups selected from halogen, cyano, nitro, OH, C$_{1-4}$ alkyloxy, C$_{3-6}$ cycloalkyl and C$_{1-4}$ alkyl optionally substituted with 1 to 5 halogen atoms, and (4) C$_{3-6}$ cycloalkyl, or R$^b$ and R$^c$ together with the nitrogen atom to which they are attached form a 4-, 5-, or 6-membered ring optionally containing an additional heteroatom selected from N, O, and S; or R$^b$ and R$^c$ together with the nitrogen atom to which they are attached form a cyclic imide;

R$^d$ is selected from (1) C$_{1-4}$ alkyl optionally substituted with 1 to 5 halogen atoms, (2) C$_{1-4}$ alkyloxy, (3) phenyl optionally substituted with 1 to 3 groups selected from halogen, cyano, nitro, OH, C$_{1-4}$ alkyloxy, C$_{3-6}$ cycloalkyl and C$_{1-4}$ alkyl optionally substituted with 1 to 5 halogen atoms, and (4) hydrogen;

X is selected from CH and N;

Y is selected from C and S=O; and k is selected from 0, 1, and 2.

For compounds of formula I, examples of R$^1$ and R$^2$ include hydrogen, methyl, ethyl, n-propyl, isopropyl, n-butyl, t-butyl, isobutyl and sec-butyl. In one embodiment of formula I are compounds wherein R$^1$ and R$^2$ are each hydrogen.

Examples of R$^{3a}$ and R$^{3b}$ for compounds of formula I include hydrogen, methyl, ethyl, n-propyl, isopropyl, n-butyl, t-butyl, isobutyl, sec-butyl, chloromethyl, fluoromethyl, trifluoromethyl, 2,2,2-trifluoroethyl, 2,2-difluoroethyl, 1,1,2,2,2-pentafluoroethyl, and the like. In one embodiment of formula I are compounds wherein one of R$^{3a}$ and R$^{3b}$ is hydrogen and the other is hydrogen or C$_{1-4}$ alkyl. In one subset R$^{3a}$ and R$^{3b}$ are each hydrogen, and in another subset one of R$^{3a}$ and R$^{3b}$ is hydrogen and the other methyl.

Examples of R$^{4a}$ and R$^{4b}$ for compounds of formula I include hydrogen, methyl, ethyl, n-propyl, isopropyl, n-butyl, sec-butyl, isobutyl, t-butyl, chlorine, fluorine, bromine, chloromethyl, 1-chloroethyl, hydroxymethyl, 2-methoxyethyl, ethoxymethyl, acetyloxymethyl, methylthiomethyl, aminomethyl, methylaminomethyl, (dimethylamino)methyl, (methylsulfonyl)oxymethyl, and the like. In one embodiment of formula I are compounds wherein one of R$^{4a}$ and R$^{4b}$ is hydrogen and the other is selected from hydrogen, halogen and C$_{1-4}$ alkyl optionally substituted with a group selected from halogen, OR$^a$, OC(O)R$^a$, S(O)$_k$R$^d$, OS(O)$_2$R$^d$, and NR$^1$R$^2$, or R$^{4a}$ and R$^{4b}$ together with the carbon atom to which they are both attached form an exo-cyclic methylene. In one subset R$^{4a}$ and R$^{4b}$ are each hydrogen; in another subset R$^{4a}$ is hydrogen and R$^{4b}$ is selected from CH$_2$-halogen, CH$_2$—OR$^a$, CH$_2$—OC(O)R$^a$, CH$_2$—S(O)$_k$R$^d$, CH$_2$—OS(O)$_2$R$^d$, and CH$_2$—NR$^1$R$^2$; in a further subset R$^{4a}$ is hydrogen and R$^{4b}$ is selected from hydroxymethyl, acetyloxymethyl, chloromethyl, (methanesulfonyl)oxymethyl, (methylthio)methyl and (dimethylamino)methyl.

Examples of R$^5$ for compounds of formula I include methyl, ethyl, n-propyl, isopropyl, n-butyl, sec-butyl, isobutyl, t-butyl, chloromethyl, 1-chloroethyl, trifluoromethyl, 2,2,2-trifluoroethyl, cyanomethyl, 1-hydroxypropyl, isopropyl, methoxymethyl, 3-methoxy-3-oxopropyl, isobutyl, 2-phenyl-ethyl, 1-ethylpropyl, phenylthiomethyl, phenoxymethyl, 2,2-dimethylpropyl, 2-cyclopentylethyl, 2-methoxy-2-oxoethyl, 2-methoxyethyl, ethoxymethyl, 2-nitroethyl, 1-cyanocyclopropyl, cyclopropyl, cyclopentyl, 2-phenylcyclopropyl, allyl, 3-butynyl, propargyl, phenyl, benzyl, 3,5-bis(trifluoromethyl)phenyl, 2,4-difluorophenyl, 4-methylphenyl, 3,4-dimethoxybenzyl, 3,4-dimethoxyphenyl, 4-cyanophenyl, 3-nitrophenyl, 2-naphthyl, 3,4-methylenedioxyphenyl, 3-cyanophenyl, 2-cyanophenyl, 3-fluorophenyl, 3-methoxyphenyl, 3-chlorophenyl, 3,4-dichlorophenyl, 3,5-dimethoxyphenyl, 3-trifluoromethylphenyl, 3-methylphenyl, 3,5-dichlorophenyl, 3-hydroxyphenyl, 3-nitro-5-(trifluoromethyl)phenyl, 5-isoxazolyl, 2-benzothienyl, 2-thienylmethyl, 3-pyridyl, 4-pyridyl, 2-furyl, 2-thienyl, 5-methyl-3-isoxazolyl, 3-tetrahydrofuranyl, 4-methyl-1,2,5-oxadiazol-3-yl, 6-hydroxy-2-pyridyl, 6-chloro-2-pyridyl, 1-methyl-4-pyrazolyl, 1-pyrazolylmethyl, 1-methyl-2-imidazolyl, 1,2,4-triazol-1-ylmethyl, 4-thiazolyl, 5-oxo-tetra-hydrofuran-2-yl, 2-oxo-5-pyranyl, 3-isoxazolyl, 3-pyridazinyl, 5-pyrimidinyl, 4-pyrimidinyl, 1-imidazolylmethyl, 1-methyl-5-pyrazolyl, 1-methyl-3-pyrazolyl, 5-thiazolyl, 5-methyl-1-pyrazolylmethyl, (3-methyl-1,2,4-triazol-5-yl)methyl, 2-(1,2,4-triazol-1-yl)ethyl, 5-methyl-4-thiazolyl, 5-methyl-3-pyridyl, 2quinoxalinyl, 2-chloro-3-pyridyl, 5-bromo-3-pyridyl, and 5-hydroxy-3-pyridyl.

In one embodiment of formula I are compounds wherein R$^5$ is C$_{1-6}$ alkyl optionally substituted with 1 to 5 groups independently selected from halogen, nitro, cyano, OR$^a$, SR$^a$, COR$^a$, SO$_2$R$^d$, CO$_2$R$^a$, OC(O)R$^a$, NR$^b$R$^c$, NR$^b$C(O)R$^a$, C(O)NR$^b$R$^c$, C$_{3-8}$ cycloalkyl. In one subset are compounds wherein R$^5$ is C$_{1-5}$ alkyl optionally substituted with 1 to 5 groups independently selected from halogen, nitro, cyano, OR$^a$, SR$^a$, CO$_2$R$^a$ and C$_{3-8}$ cycloalkyl. In a further subset are compounds wherein R$^5$ is selected from C$_{1-5}$ alkyl and C$_{1-3}$ alkyl substituted with 1 to 3 groups selected from halogen, cyano, hydroxy, C$_{1-4}$ alkoxy and C$_{1-4}$ alkoxycarbonyl.

In another embodiment of formula I are compounds wherein R$^5$ is C$_{3-6}$ cycloalkyl optionally substituted with 1 to 3 groups independently selected from halogen, nitro, cyano and phenyl. In one subset R$^5$ is C$_{3-6}$ cycloalkyl optionally substituted with a group selected from cyano and phenyl.

In another embodiment of formula I are compounds wherein R$^5$ is (CH$_2$)$_k$-heterocycle optionally substituted with 1 to 2 groups independently selected from halogen, nitro, cyano, OR$^a$, SR$^a$, C$_{1-4}$ alkyl and C$_{1-3}$ haloalkyl wherein said heterocycle is selected from isoxazolyl, thienyl, pyridinyl, benzothienyl, furyl, tetrahydrofuranyl, oxadiazolyl, 1-oxidopyridinyl, pyrazolyl, imidazolyl, 1,2,4-triazolyl, thiazolyl, 5-oxotetrahydrofuranyl, 2-oxo-2H-pyranyl, 6-oxo-1,6-dihydropyridazinyl, oxazolyl, pyridazinyl, pyrimidinyl and quinoxalinyl. In one subset R$^5$ is selected from isoxazolyl optionally substituted with 1 or 2 C$_{1-4}$ alkyl, thienyl, pyridinyl optionally substituted with hydroxy or halogen, benzothienyl, furyl, tetrahydrofuranyl, oxadiazolyl optionally substituted with C$_{1-4}$ alkyl, 1-oxidopyridinyl optionally substituted with C$_{1-4}$ alkyl, pyrazolyl optionally substituted with C$_{1-4}$ alkyl, imidazolyl optionally substituted with C$_{1-4}$ alkyl, 1,2,4-triazolyl optionally substituted with C$_{1-4}$ alkyl, thiazolyl optionally substituted with C$_{1-4}$ alkyl, 5-oxotetrahydrofuranyl, 2-oxo-2H-pyranyl, 6-oxo-1,6-dihydropyridazinyl, oxazolyl, pyridazinyl, pyrimidinyl and quinoxalinyl.

For compounds of formula I examples of R$^{6a}$ include trifluoromethanesulfonyloxy, methanesulfonyloxy, ethanesulfonyloxy, propanesulfonyloxy, isopropanesulfonyloxy, benzenesulfonyloxy, phenylmethanesulfonyloxy, dimethylsulfamoyloxy, methylsulfonylamino, N-(methyl)-trifluoromethylsulfonylmethyl, methylsulfonylamino, trifluoromethylsulfonylamino, and

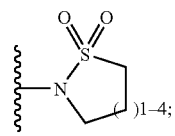

where R$^{6a}$ and R$^{6b}$ are attached to adjacent atoms and R$^{6a}$ is R$^{8a}$SO$_2$R$^9$ then R$^{6a}$ and R$^{6b}$ together with the benzene ring to which they are attached may represent N-sulfonyl-8-tetrahydroquinolyl. Examples of R$^{6b}$ include hydrogen, chloro, fluoro, methyl, methoxy, methoxycarbonyl, and OSO$_2$CF$_3$; examples of R$^{6c}$ and R$^{6d}$ include hydrogen, chloro, fluoro, methyl, methoxy, and methoxycarbonyl; an example where R$^{6c}$ and R$^{6d}$ together with the carbons to which they are attached form a ring is benzene; and examples of R$^7$ include hydrogen, fluorine, chlorine, methoxy, and methoxycarbonyl.

In another embodiment of formula I are compounds represented by formula I(1):

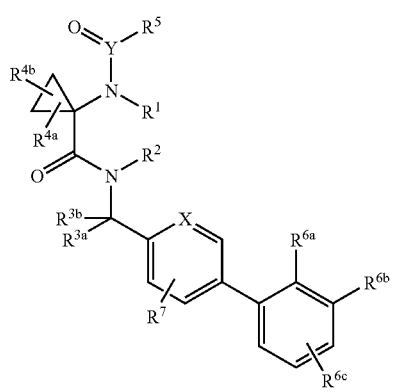

I(1)

wherein X, Y, R$^1$, R$^2$, R$^{3a}$, R$^{3b}$, R$^{4a}$, R$^{4b}$, R$^5$, R$^{6a}$, R$^{6b}$, R$^{6c}$, and R$^7$ have the same definitions as provided under formula I.

In one subset of formula I(1) are compounds wherein R$^{6b}$ is selected from hydrogen, halogen and OSO$_2$R$^8$. In one subgroup R$^{6b}$ is fluorine or chlorine.

In another subset of formula I(1), R$^{6c}$ is hydrogen or halogen.

In another subset of formula I(1), R$^{6a}$ is OSO$_2$R$^8$ or NHSO$_2$R$^9$. In one subgroup R$^{6a}$ is NHSO$_2$R$^9$, and R$^9$ is C$_{1-4}$ alkyl optionally substituted with 1 to 5 halogen atoms.

In another subset of formula I(1), R$^7$ is hydrogen or halogen. In one subgroup, R$^7$ is hydrogen. In another subgroup, R7 is fluorine. In yet another subgroup, R$^7$ is chlorine.

In another subset of formula I(1) are compounds wherein R$^{6a}$ is OSO$_2$R$^8$ and R$^8$ is selected from methyl, trifluoromethyl, ethyl, propyl, isopropyl, benzyl, dimethylamino, 2,2,2-trifluoroethyl, and phenyl.

In another embodiment of formula I are compounds represented by formula I(2):

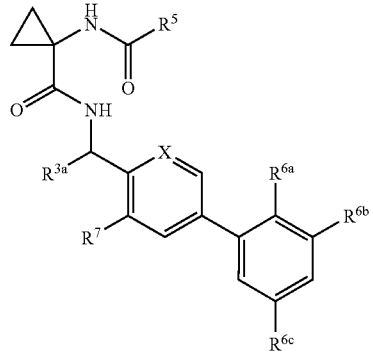

I(2)

wherein X is N or CH, R$^{3a}$ is H or C$_{1-4}$ alkyl, R$^7$ is hydrogen or halogen, and R$^5$, R$^{6a}$, R$^{6b}$ and R$^{6c}$ have the same definitions as provided under formula I.

In one subset of formula I(2), R$^{6a}$ is NHSO$_2$R$^9$. In one subgroup R$^9$ is C$_{1-4}$ alkyl optionally substituted with 1 to 5 halogen atoms, R$^{6b}$ is halogen, and R$^{6c}$ is hydrogen or halogen. In another subgroup R$^9$ is methyl or trifluoromethyl, R$^{6b}$ is halogen, and R$^{6c}$ is hydrogen.

In another subset of formula I(2), R$^{6a}$ is OSO$_2$R$^8$. In one subgroup R$^8$ is selected from methyl, trifluoromethyl, ethyl, propyl, isopropyl, benzyl, dimethylamino, 2,2,2-trifluoroethyl, and phenyl; R$^{6b}$ is hydrogen or halogen, and R$^{6c}$ is hydrogen or halogen.

Some representative compounds of the instant invention are:
3,3'-difluoro-4'-{[({1-[(pyrimidin-5-ylcarbonyl)amino]cyclopropyl}carbonyl)amino]methyl}-1,1'-biphenyl-2-yl trifluoromethanesulfonate,
3,3'-difluoro-4'-{(1R)-1-[({1-[(trifluoroacetyl)amino]cyclopropyl}carbonyl)amino]ethyl}-1,1'-biphenyl-2-yl trifluoromethanesulfonate,
3,3'-difluoro-4'-((1R)-1-{[(1-{[(trifluoromethyl)sulfonyl]amino}cyclopropyl)carbonyl]amino}ethyl)-1,1'-biphenyl-2-yl trifluoromethanesulfonate,
1-({[(1R)-1-(3,3'-difluoro-2'-{[(trifluoromethyl)sulfonyl]oxy}-1,1'-biphenyl-4-yl)ethyl]amino}carbonyl)cyclopropanaminium trifluoroacetate,
3,3'-difluoro-4'-{(1R)-1-[({1-[(trifluoroacetyl)amino]cyclopropyl}carbonyl)amino]ethyl}-1,1'-biphenyl-2-yl methanesulfonate,
5-chloro-3,3'-difluoro-4'-{(1R)-1-[({1-[(trifluoroacetyl)amino]cyclopropyl}carbonyl)amino]ethyl}-1,1'-biphenyl-2-yl trifluoromethanesulfonate, 3,3'-difluoro-4'-{(1R)-1-[({1-[(trifluoroacetyl)amino]
cyclopropyl}carbonyl)amino]ethyl}1,1,1'-biphenyl-2-yl
ethanesulfonate,
3,3'-difluoro-4'-{(1R)-1-[({1-[(trifluoroacetyl)amino]
cyclopropyl}carbonyl)amino]ethyl}-1,1'-biphenyl-2-yl
propane-1-sulfonate,
3,3'-difluoro-4'-{(1R)-1-[({1-[(trifluoroacetyl)amino]
cyclopropyl}carbonyl)amino]ethyl}-1,1'-biphenyl-2-yl
propane-2-sulfonate,
3,3'-difluoro-4'-{(1R)-1-[({1-[(trifluoroacetyl)amino]
cyclopropyl}carbonyl)amino]ethyl}-1,1'-biphenyl-2-yl
benzenesulfonate,
3,3'-difluoro-4'-{(1R)-1-[({1-[(trifluoroacetyl)amino]
cyclopropyl}carbonyl)amino]ethyl}-1,1'-biphenyl-2-yl
phenylmethanesulfonate,
3,3'-difluoro-4'-{(1R)-1-[({1-[(trifluoroacetyl)amino]
cyclopropyl}carbonyl)amino]ethyl}-1,1'-biphenyl-2-yl
dimethylsulfamate,
3,3'-difluoro-4'-{(1R)-1-[({1-[(trifluoroacetyl)amino]
cyclopropyl}carbonyl)amino]ethyl}-1,1'-biphenyl-2-yl
2,2,2-trifluoroethanesulfonate,
3-chloro-3'-fluoro-4'-{(1R)-1-[({1-[(trifluoroacetyl)amino]
cyclopropyl}carbonyl)amino]ethyl}-1,1'-biphenyl-2-yl
trifluoromethanesulfonate,
3'-fluoro-4'-{(1R)-1-[({1-[(trifluoroacetyl)amino]
cyclopropyl}carbonyl)amino]ethyl}-2-{[(trifluorom-
ethyl)sulfonyl]oxy}-1,1'-biphenyl-3-yl trifluoromethane-
sulfonate,
N-(1-{[((1R)-1-{3,3'-difluoro-2'-[methyl(methylsulfonyl)
amino]-1,1'-biphenyl-4-yl}ethyl)amino]-
carbonyl}cyclopropyl)pyrimidine-5-carboxamide,
N-(1-{[({3,3'-difluoro-2'-[(methylsulfonyl)amino]-1,1'-bi-
phenyl-4-yl}methyl)amino]carbonyl}-cyclopropyl)pyri-
midine-5-carboxamide,
N-{1-[({[2'-(1,1-dioxido-1,2-thiazinan-2-yl)-3,3'-difluoro-
1,1'-biphenyl-4-yl]methyl}amino)carbonyl]-
cyclopropyl}pyrimidine-5-carboxamide,
N-[(1R)-1-(3,3'-difluoro-2'-{[(trifluoromethyl)sulfonyl]me-
thyl}-1,1'-biphenyl-4-yl)ethyl]-1-[(trifluoroacetyl)amino]
cyclopropanecarboxamide,
N-[(1R)-1-(3,3'-difluoro-2'-{[(trifluoromethyl)sulfonyl]
amino}-1,1'-biphenyl-4-yl)ethyl]-1-[(trifluoroacetyl)
amino]cyclopropanecarboxamide, and
N-(1-{[((1R)-1-{3,3'-difluoro-2'-[(methylsulfonyl)amino]-
1,1'-biphenyl-4-yl}ethyl)amino]carbonyl}-cyclopropyl)
pyrimidine-5-carboxamide.

Unless otherwise stated, the following terms have the meanings indicated below:

"Alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like.

"Alkenyl" means a linear or branched carbon chain containing at least one C=C bond. Examples of alkenyl include allyl, 2-butenyl, 3-butenyl, 1-methyl-2-propenyl, and the like.

"Alkynyl" means a linear or branched carbon chain containing at least one C≡C bond. Examples of alkynyl include propargyl, 2-butynyl, 3-butynyl, 1-methyl-2-propy-nyl, and the like.

"Aryl" means carbocyclic aromatic ring systems. Examples of aryl include phenyl and napthyl.

"Cyclic imide" includes succinimide, maleimide, phthal-imide and the like.

"Cycloalkyl" means carbocycles containing no heteroat-oms, and includes mono-, bi- and tricyclic saturated car-bocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adaman-tane, indanyl, indenyl, fluorenyl, 1,2,3,4-tetrahydronaphtha-lene and the like.

"Haloalkyl" means an alkyl radical as defined above wherein at least one and up to all of the hydrogen atoms are replaced with a halogen. Examples of such haloalkyl radi-cals include chloromethyl, 1-bromoethyl, fluoromethyl, dif-luoromethyl, trifluoromethyl, 2,2,2-trifluoroethyl and the like.

"Halogen" means fluorine, chlorine, bromine and iodine.

"Optionally substituted" is intended to include both sub-stituted and unsubstituted. Thus, for example, optionally substituted aryl could represent a pentafluorophenyl or a phenyl ring.

Optical Isomers—Diastereomers—Geometric Isomers—Tautomers

Compounds described herein may contain an asymmetric center and may thus exist as enantiomers. Where the com-pounds according to the invention possess two or more asymmetric centers, they may additionally exist as diaste-reomers. The present invention includes all such possible stereoisomers as substantially pure resolved enantiomers, racemic mixtures thereof, as well as mixtures of diastere-omers. The above Formula I is shown without a definitive stereochemistry at certain positions. The present invention includes all stereoisomers of Formula I and pharmaceuti-cally acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tau-tomers as well as mixture thereof are encompassed with compounds of Formula I.

Salts

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, includ-ing inorganic bases and organic bases. Salts derived from such inorganic bases include aluminum, ammonium, cal-cium, copper (ic and ous), ferric, ferrous, lithium, magne-sium, manganese (ic and ous), potassium, sodium, zinc and the like salts. Preferred are the ammonium, calcium, mag-nesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N-dibenzylethylenediamine, diethylamine, 2-diethylaminoethanol, 2Aimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

Prodrugs

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a nonaqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water.

A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The following are examples of representative pharmaceutical dosage forms for the compounds of Formula I:

B1 receptor, and as such are useful in the treatment and prevention of diseases and conditions mediated through the bradykinin receptor pathway such as pain and inflammation. The compounds would be effective in the treatment or prevention of pain including, for example, visceral pain (such as pancreatitis, interstitial cystitis, renal colic, prostatitis, chronic pelvic pain), neuropathic pain (such as postherpetic neuralgia, acute zoster pain, nerve injury, the "dynias", e.g., vulvodynia, phantom limb pain, root avulsions, radiculopathy, painful traumatic mononeuropathy, painful entrapment neuropathy, carpal tunnel syndrome, ulnar neuropathy, tarsal tunnel syndrome, painful diabetic neuropathy, painful polyneuropathy, trigeminal neuralgia), central pain syndromes (potentially caused by virtually any lesion at any level of the nervous system including but not limited to stroke, multiple sclerosis, spinal cord injury), and postsurgical pain syndromes (e.g., postmastectomy syndrome, postthoracotomy syndrome, stump pain)), bone and joint pain (osteoarthritis), spine pain (e.g., acute and chronic low back pain, neck pain, spinal stenosis), shoulder pain, repetitive motion pain, dental pain, sore throat, cancer pain, myofascial pain (muscular injury, fibromyalgia), postoperative, perioperative pain and preemptive analgesia (including but not limited to general surgery, orthopedic, and gynecological), chronic pain, dysmenorrhea (primary and secodnary), as well as pain associated with angina, and inflammatory pain of varied origins (e.g. osteoarthritis, rheumatoid arthritis, rheumatic disease, teno-synovitis and gout, ankylosing spondylitis, bursitis).

Further, the compounds of this invention can also be used to treat hyperreactive airways and to treat inflammatory events associated with airways disease e.g. asthma including allergic asthma (atopic or non-atopic) as well as exercise-induced bronchoconstriction, occupational asthma, viral- or bacterial exacerbation of asthma, other non-allergic asthmas and "wheezy-infant syndrome". Compounds of the present invention may also be used to treat chronic obstructive pulmonary disease including emphysema, adult respiratory distress syndrome, bronchitis, pneumonia, allergic rhinitis (seasonal and perennial), and vasomotor rhinitis. They may also be effective against pneumoconiosis, including aluminosis, anthracosis, asbestosis, chalicosis, ptilosis, siderosis, silicosis, tabacosis and byssinosis.

Compounds of the present invention may also be used for the treatment of inflammatory bowel disease including Crohn's disease and ulcerative colitis, irritable bowel syndrome, pancreatitis, nephritis, cystitis (interstitial cystitis), uveitis, inflammatory skin disorders such as psoriasis and eczema, rheumatoid arthritis and edema resulting from trauma associated with burns, sprains or fracture, cerebral edema and angioedema. They may be used to treat diabetic vasculopathy, diabetic neuropathy, diabetic retinopathy, post

| Inj. Suspension (I.M.) | mg/mL | Tablet | mg/tab. | Capsule | mg/cap. |
|---|---|---|---|---|---|
| Cmpd of Formula I | 10 | Cmpd of Formula I | 25 | Cmpd of Formula I | 25 |
| Methylcellulose | 5.0 | Microcryst. Cellulose | 415 | Lactose Powder | 573.5 |
| Tween 80 | 0.5 | Povidone | 14.0 | Magnesium Stearate | 1.5 |
| Benzyl alcohol | 9.0 | Pregelatinized Starch | 43.5 | | 600 |
| Benzalkonium chloride | 1.0 | Magnesium Stearate | 2.5 | | |
| Water for injection to a total volume of 1 mL | | | 500 | | |

Utilities

Compounds of this invention are antagonists or inverse agonists of bradykinin receptor, in particular the bradykinin capillary resistance or diabetic symptoms associated with insulitis (e.g. hyperglycemia, diuresis, proteinuria and increased nitrite and kallrein urinary excretion). They may be used as smooth muscle relaxants for the treatment of spasm of the gastrointestinal tract or uterus. Additionally, they may be effective against liver disease, multiple sclerosis, cardiovascular disease, e.g. atherosclerosis, congestive heart failure, myocardial infarct; neurodegenerative diseases, e.g. Parkinson's and Alzheimers disease, epilepsy, septic shock e.g. as anti-hypovolemic and/or anti-hypotensive agents, headache including cluster headache, migraine including prophylactic and acute use, stroke, closed head trauma, cancer, sepsis, gingivitis, osteoporosis, benign prostatic hyperplasia and hyperactive bladder. Animal models of these diseases and conditions are generally well known in the art, and may be suitable for evaluating compounds of the present invention for their potential utilities. Finally, compounds of the present invention are also useful as research tools (in vivo and in vitro).

Compounds of the present invention are also useful as research tools (in vivo, in vitro and ex vivo). In one aspect a compound of the present invention is labeled with a radionuclide, preferably $^{35}$S, and used in a brain receptor occupancy assay to assess the ability of test compounds to penetrate the blood brain barrier as well as the ability to distribute into the tissue and bind to the receptor. One such receptor occupancy assay using transgenic animal expressing human bradykinin B1 receptor is described hereinbelow.

The compounds of this invention are useful in the treatment of pain and inflammation by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

The compounds would be effective in the treatment or prevention of pain including, for example, bone and joint pain (osteoarthritis), repetitive motion pain, dental pain, cancer pain, myofascial pain (muscular injury, fibromyalgia), perioperative pain (general surgery, oral surgery, gynecological), neuropathic pain (post-herpetic neuralgia), and chronic pain by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

In particular, inflammatory pain such as, for example, inflammatory airways disease (chronic obstructive pulmonary disease) would be effectively treated by the compounds of this invention by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Further, the compounds of this invention can additionally be used to treat asthma, inflammatory bowel disease, rhinitis, pancreatitis, cystitis (interstitial cystitis), uveitis, inflammatory skin disorders, rheumatoid arthritis and edema resulting from trauma associated with burns, sprains or fracture by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used subsequent to surgical intervention (e.g. as post-operative analgesics) and to treat inflammatory pain of varied origins (e.g. osteoarthritis, rheumatoid arthritis, rheumatic disease, teno-synovitis and gout) as well as for the treatment of pain associated with angina, menstruation or cancer by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat diabetic vasculopathy, post capillary resistance or diabetic symptoms associated with insulitis (e.g. hyperglycemia, diuresis, proteinuria and increased nitrite and kallikrein urinary excretion) by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat inflammatory skin disorders such as psoriasis and eczema by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used as smooth muscle relaxants for the treatment of spasm of the gastrointestinal tract or uterus or in the therapy of Crohn's disease, ulcerative colitis or pancreatitis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Such compounds may be used therapeutically to treat hyperreactive airways and to treat inflammatory events associated with airways disease e.g. asthma, and to control, restrict or reverse airways hyperreactivity in asthma by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat intrinsic and extrinsic asthma including allergic asthma (atopic or non-atopic) as well as exercise-induced bronchoconstriction, occupational asthma, viral or bacterial exacerbated asthma, other non-allergic asthmas and "wheezy-infant syndrome" by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may also be effective against pneumoconiosis, including aluminosis, anthracosis, asbestosis, chalicosis, ptilosis, siderosis, silicosis, tabacosis and byssinosis was well as adult respiratory distress syndrome, chronic obstructive pulmonary or airways disease, bronchitis, allergic rhinitis, and vasomotor rhinitis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Additionally, they may be effective against liver disease, multiple sclerosis, atherosclerosis, Alzheimer's disease, septic shock e.g. as anti-hypovolemic and/or anti-hypotensive agents, cerebral edema, headache including cluster headache, migraine including prophylactic and acute use, closed head trauma, irritable bowel syndrome and nephritis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (1) morphine and other opiate receptor agonists including propoxyphene (Darvon) and tramadol; (2) non-steroidal antiinflammatory drugs (NSAIDs) including COX-2 inhibitors such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib); (3) corticosteroids such as betamethasone, budesonide, cortisone, dexamethasone, hydrocortisone, methylprednisolone, prednisolone, prednisone and triamcinolone; (4) histamine H1 receptor antagonists such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, desloratadine, fexofenadine and levocetirizine; (5) histamine H2 receptor antagonists such as cimetidine, famotidine and ranitidine; (6) proton pump inhibitors such as omeprazole, pantoprazole and esomeprazole; (7) leukotriene antagonists and 5-lipoxygenase inhibitors such as zafirlukast; montelukast, pranlukast and zileuton; (8) drugs used for angina, myocardial ischemia including nitrates such as nitroglycerin and isosorbide nitrates, beta blockers such as atenolol, metoprolol, propranolol, acebutolol ,betaxolol, bisoprolol, carteolol, labetalol, nadolol, oxprenolol, penbutolol, pindolol, sotalol and timolol, and calcium channel blockers such as diltiazam, verapamil, nifedipine, bepridil, felodipine, flunarizine, isradipine, nicardipine and nimodipine; (9) incontinence medications such as antimuscarinics, e.g., tolterodine and okybutinin); (10) gastrointestinal antispasmodics (such as atropine, scopolamine, dicyclomine, antimuscarinics, as well as diphenoxylate); skeletal muscle relaxants (cyclobenzaprine, carisoprodol, chlorphenesin, chlorzoxazone, metaxalone, methocarbamol, baclofen, dantrolene, diazepam, or orphenadrine); (11) gout medications such as allopurinol, probenicid and colchicine; (12) drugs for rheumatoid arthritis such as methotrexate, auranofin, aurothioglucose and gold sodium thiomalate; (13) drugs for osteoporosis such as alendronate and raloxifene; decongestants such as pseudoephedrine and phenylpropanolamine; (14) local anesthetics; (15) anti-herpes drugs such as acyclovir, valacyclovir and famcyclovir; (16) anti-emetics such as ondansetron and granisetron; (17) migraine drugs such as the triptans (e.g. rizatriptan, sumatriptan), ergotamine, dihydroergotamine, CGRP antagonists, antidepressants (e.g., tricyclic antidepressants, serotonin-selective reuptake inhibitors, beta-adrenergic blockers); (18) VR1 antagonsits; (19) anticonvulsants (e.g., gabapentin, pregabalin, lamotrigine, topiramate, carbamazepine, oxcarbazepine, phenyloin); (20) glutamate antagonists (e.g., ketamine and other NMDA antagonists, NR2B antagonists); (21) acetaminophen; (22) CCR2 antagonists; (23) PDE4 antagonists Biological Evaluation Assessing the Affinity of Selected Compounds to Bind to the Bradykinin B1 or B2 Receptor Radioligand binding assays are performed using membranes from CHO cells that stably express the human, rabbit, rat, or dog B1 receptors or CHO cells that express the human B2 receptor. For all receptor types, cells are harvested from culture flasks in PBS/1 mM EDTA and centrifuged at 1000×g for 10 minutes. The cell pellets are homogenized with a polytron in ice cold 20 mM HEPES, 1 mM EDTA, pH 7.4 (lysis buffer) and centrifuged at 20,000×g for 20 minutes. The membrane pellets are rehomogenized in lysis buffer, centrifuged again at 20,000×g and the final pellets are resuspended at 5 mg protein/ml in assay buffer (120 mM NaCl, 5 mM KCl, 20 mM BEPES, pH 7.4) supplemented with 1% BSA and frozen at −80° C.

On the day of assay, membranes are centrifuged at 14,000×g for 5 minutes and resuspended to the desired protein concentration in assay buffer containing 100 nM enaliprilat, 140 µg/mL bacitracin and 0.1% BSA. 3H-des-arg10, leu9 kallidin is the radioligand used for the human and rabbit B1 receptors, 3H-des-arg10 kallidin is used for the rat and dog B1 receptors, and 3H-bradykinin is used to label the human B2 receptor.

For all assays, compounds are diluted from DMSO stock solutions with 4 µL added to assay tubes for a final DMSO concentration of 2%. This is followed by the addition of 100 µL radioligand and 100 µL of the membrane suspension. Nonspecific binding for the B1 receptor binding assays is determined using 1 µM des-arg10 kallidin and nonspecific binding for the B2 receptor is determined with 1 µM bradykinin. Tubes are incubated at room temperature (22° C.) for 60 minutes followed by filtration using a Tomtec 96-well harvesting system. Radioactivity retained by the filter is counted using a Wallac Beta-plate scintillation counter.

The compounds of this invention have affinity for the B1 receptor in the above assay as demonstrated by results of less than 5 μM. It is advantageous that the assay results be less than 1 μM, even more advantageous for the results be less than 0.5 μM. It is further advantageous that compounds of this invention have affinity for the bradykinin B1 receptor over the bradykinin B2 receptor; more advantageously, the affinity for the B1 receptor is at least 10 fold, and preferably over 100 fold, over that for the B2 receptor.

Assay for Bradykinin B1 Antagonists

B1 agonist-induced calcium mobilization was monitored using a Fluorescence Imaging Plate Reader (FLIPR). CHO cells expressing the B1 receptor were plated in 96 or 384 well plates and allowed to incubate in Iscove's modified DMEM overnight. Wells were washed two times with a physiological buffered salt solution and then incubated with 4 uM Fluo-3 for one hour at 37° C. The plates were then washed two times with buffered salt solution and 100 uL of buffer was added to each well. Plates were placed in the FLIPR unit and allowed to equilibrate for two minutes. The test compound was then added in 50 ul volumes followed five minutes later by 50 ul of agonist (des-arg$^{10}$ kallidin). Relative fluorescence peak heights in the absence and presence of antagonist were used to calculate the degree of inhibition of the B1 receptor agonist response by the test compound. Eight to ten concentrations of test compound were typically evaluated to construct an inhibition curve and determine IC50 values using a four-parameter nonlinear regression curve fitting routine.

Assay for Bradykinin Inverse Agonists

Inverse agonist activity at the human B1 receptor was evaluated using transiently transfected HEK293 cells. One day following transfection cell flasks were labeled overnight with 6 uCi/ml [$^3$H]myo-inositol. On the day of assay, the media was removed and the attached cells were gently rinsed with 2×20 ml of phosphate-buffered saline. Assay buffer (HEPES buffered physiological salts, pH 7.4) was added and the cells were detached by tapping of the flask. The cells were centrifuged at 800×g for five minutes and resuspended at 1×10$^6$ cells/ml in assay buffer supplemented with 10 nM lithium chloride. After 10 minutes at room temperature, one-half ml aliquots were distributed to tubes containing test compound or vehicle. After an additional 10 minutes the tubes were transferred to a 37° C. water bath for 30 minutes. The incubation was terminated by the addition of a 12% perchloric acid solution and the tubes were placed on ice for 30 minutes. The acid was then neutralized with KOH and the tubes centrifuged to pellet precipitated material. [$^3$H]Inositol monophosphate formed was recovered by standard ion exchange chromatographic techniques and quantitated by liquid scintillation counting. Inverse agonist activity was determined by the degree to which a test compound reduced basal (cells incubated with vehicle) levels of [$^3$H]inositol monophosphate accumulation.

Ex vivo Receptor Occupancy Assay in NSE_hB$_1$ transgenic rat

Transgenic rats of either sex are placed in an induction chamber and anesthetized with isoflurane under a Flow Sciences hood. Once anesthetized, the rat is placed on a circulating water warning blanket (Gaymar T-pump) and anesthesia is maintained using 2% isoflurane by means of a nose cone. The tail vein is cannulated with a 25G winged infusion set-up connected to a syringe containing either test compound or vehicle. The desired dose of test compound is administered. At the experimental end-point a blood sample is taken, the rat is euthanized, and tissue is removed (typically brain and spinal cord) for subsequent assays.

For autoradiographic analysis of human B$_1$ receptor expression, tissues removed from transgenic rats were frozen on dry ice powder, and stored at −70° C. Coronal sections of the brain and the transverse sections of the spinal cord were prepared with cryostat (Leica, CM3050) at 20 TM of each. The frozen sections were stored at −70° C. For analysis, frozen sections were warmed at room temperature (RT) for 15 minutes, then followed by 15 minutes preincubation in the buffer without radioligand at RT. After preincubation, the sections were transferred to the incubation buffer, and incubated for 90 minutes at RT. Total binding, both non-specific and specific, was determined by incubating in buffer containing 0.3 nM [H-3] DALK. An adjacent section was utilized to determine non-specific binding, which was incubated in buffer containing 0.3 nM [H-3] DALK and 200 nM of a non-peptide receptor antagonist that exhibits high affinity and specificity for the human B$_1$ bradykinin receptor. Following the 90 minute incubation, the sections were washed three times, 3 minutes each, in buffer, rinsed in DIH$_2$O for 30 seconds at 4° C., and then dried by air blower at RT. The sections were placed against Fuji imaging plates, and exposed for a week at RT. The plates were scanned with Fuji PhosphorImager BAS 5000, and the images were analyzed with MCID M5 software.

For homogenate-based binding assay, thirty-five milligrams of frozen brain (cerebral cortex or cerebellum) or spinal cord is homogenized with a Polytron, in a large volume of ice-cold assay buffer (20 mM BEPES, 120 mM NaCl, 5 mM KCl, pH 7.4) and transferred to two chilled centrifuge tubes. To pellet membranes the tubes are centrifuged for 10 minutes at 75,000×g in a rotor pre-cooled to 4° C. The supernatant is discarded and each tube is rinsed with 20 ml ice-cold buffer and then homogenized pellets above in ice-cold assay buffer. The homogenate is pooled and added to a tube containing the radiotracer, 20 pM of a non-peptide human B$_1$ receptor antagonist that is labeled with $^{35}$S, in each tube containing 0.5 ml room temperature assay buffer. Nonspecific binding is determined by adding homogenate to tubes containing the radiotracer and 100 nM of the unlabeled non-peptide human B. receptor antagonist. At set time points (1,2,4,6,8,10 minutes) the contents of three tubes are filtered over individual 25 mm GF/B filters presoaked in 0.05% Triton X-100. The filtration step is performed by adding 4 ml ice-cold assay buffer to each of the three replicate tubes, pouring the contents over the filters, and washing each filter two times with 4 ml ice-cold-buffer. A Hoeffer FH 225V filtration manifold is used for the filtration. The nonspecific binding tubes are similarly filtered after finishing the 6 time points. Filters are transferred to 5 ml scintillation vials and counted after soaking 10 hours in 3 ml Beckman Ready Safe scintillation fluid.

The specific binding is calculated at each time point (total cpm—nonspecific cpm) and the slope of the association is determined by linear regression. Receptor occupancy in a drug treated animal is determined by the following equation:

$$\% \text{ Occupancy} = (1 - (\text{slope}_{drug}/\text{slope}_{vehicle})) \times 100$$

slope$_{drug}$ is the slope of the association rate line from a drug treated animal.

slope$_{vehicle}$ is the slope determined for a vehicle treated animal.

The transgenic rat expressing human badykinin B1 receptor is described in PCT Published Application WO03/016495.

Abbreviations Used

The following abbreviations have the meanings indicated, unless stated otherwise in the specification: BOC (boc)=t-butyloxycarbonyl; DCM=dichloromethane;

DMF=dimethylformamide; DMSO=Dimethyl sulfoxide; EDC or EDCI=1-(3-dimethylaminopropyl)₃-ethylcarbodiimide HCl; eq.=equivalent(s); ES (or ESI)–MS=electron spray ionization–mass spectroscopy; Et=ethyl; EtOAc=ethyl acetate; EtOH=ethanol; FAB-MS=fast atom bombardment-mass spectroscopy; HOAT=1-hydroxy-7-azabenzotriazole; HOBt=1-hydroxybenzotriazole hydrate; HPLC=high pressure liquid chromatography; LCMS=Liquid chromatography/mass spectroscopy; LHMDS=lithium bis(trimethylsilyl)amide; Me=methyl; MeOH=Methanol; MHz=megahertz; NEt3=triethylamine; NMR=nuclear magnetic resonance; Ph=Phenyl; TPA=trifluoroacetic acid; THF=tetrahydrofuran;

Compounds of formula I may be prepared according to the following illustrative schemes. In Scheme 1, the biphenyl derivative (3) is assembled using a Suzuki reaction between an aromatic boronic acid derivative (1), or an appropriate boronic ester derivative, and an aromatic halide (2) in the presence of a triarylphosphine, like triphenylphosphine, and a metal catalyst, like palladium acetate. The resultant cyano biphenyl intermediate (3), is then catalytically reduced to the benzylic amine derivative (4) using hydrogen and a metal, like Raney Ni, in an appropriate solvent. The amine derivative (4) is then coupled to the acid (5) using standard peptide coupling reagent combinations, like EDCI/HOBt, in an appropriate solvent, such as THF, to provide (6). The Boc protecting group is then removed by the action of an acid, like HCl, in an appropriate solvent, like MeOH, to yield an ammonium salt from which the free-base derivative (7) may be obtained using an appropriate base, like ammonia, and an appropriate solvent, like chloroform. This amine derivative (7) is then reacted with a carboxylic acid or carboxylic acid equivalent to yield title compound (Ia). Alternatively, the acid-salt of (7) can be used in the final reaction to yield title compound (Ia) provided an appropriate base is added, like triethylamine.

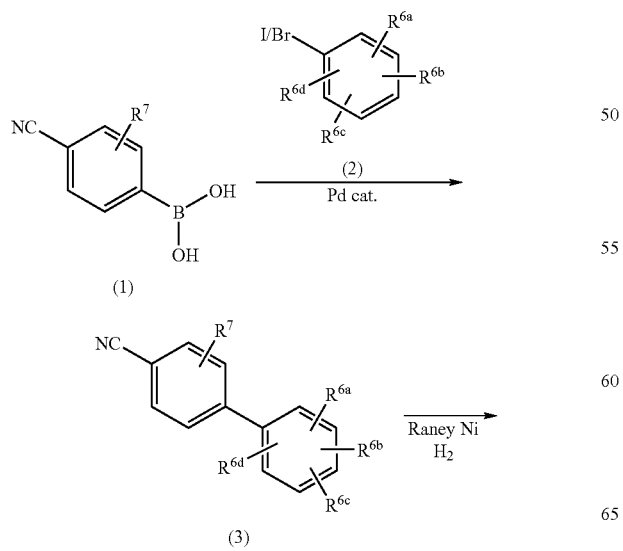

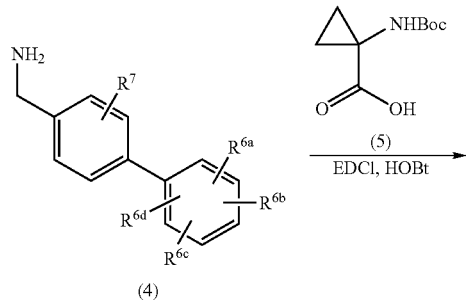

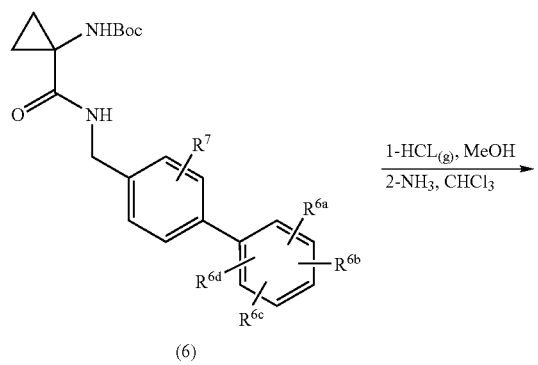

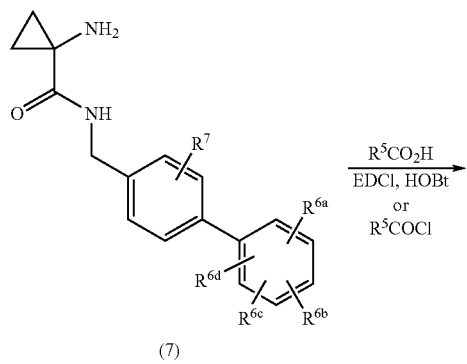

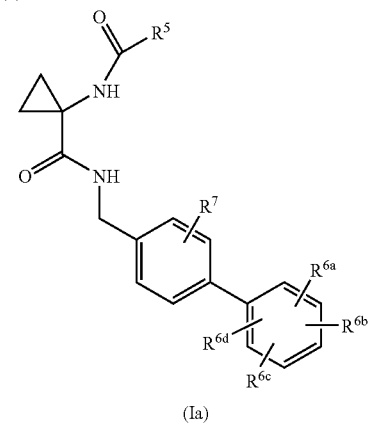

Alternatively, as illustrated in Scheme 2, a benzylic amine derivative (8), after primary amine protection with an appropriate protecting group, like Boc, is elaborated to the pinacol boron ester (10) using a palladium catalyst in an appropriate solvent, like dimethyl sulfoxide. This boron ester (10) is coupled to an aryl halide derivative (2) employing Suzuki reaction conditions to yield (11). Biphenyl (11) is elaborated to compound (12) through a standard sequence of Boc removal and peptide coupling with the cyclopropyl carboxylic acid (5). Subsequent removal of the N-terminal Boc group with hydrogen chloride and reaction of this amine hydrochloride with a carboxylic acid or carboxylic acid equivalent, in the presence of an appropriate base, like triethylamine, provides title compound (Ib)

SCHEME 2

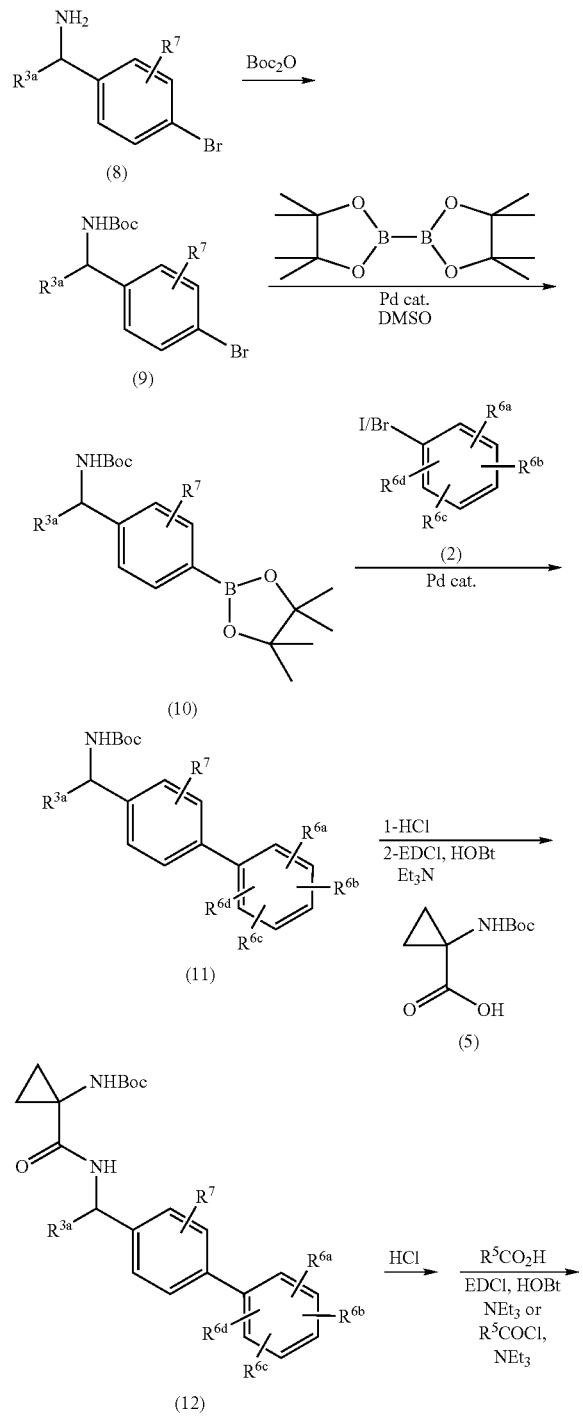

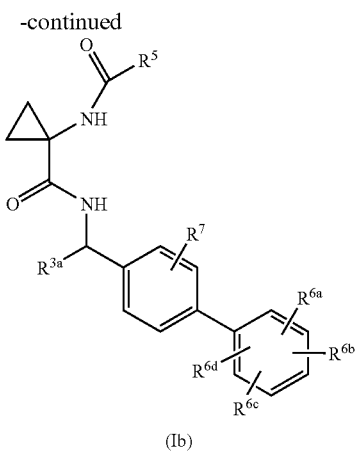

(Ib)

Alternatively, as illustrated in Scheme 3, N-Boc protected compound (12), prepared according to Scheme 2, is deprotected using strong acid, like HCl, and the resulting salt is converted to the corresponding free base using ammonia, in an appropriate solvent, like chloroform, to give the amine (15). This amine is then alkylated with excess alkyl iodide (1-$R^1$) in an appropriate solvent, like THP, in the presence of an acid scavenger, like triethylamine, at elevated temperatures to provide (16), along with bis-alkylated material. Secondary amine (16) is then converted to the title compound by reacting with a carboxylic acid or carboxylic acid equivalent to provide (Ie).

SCHEME 3

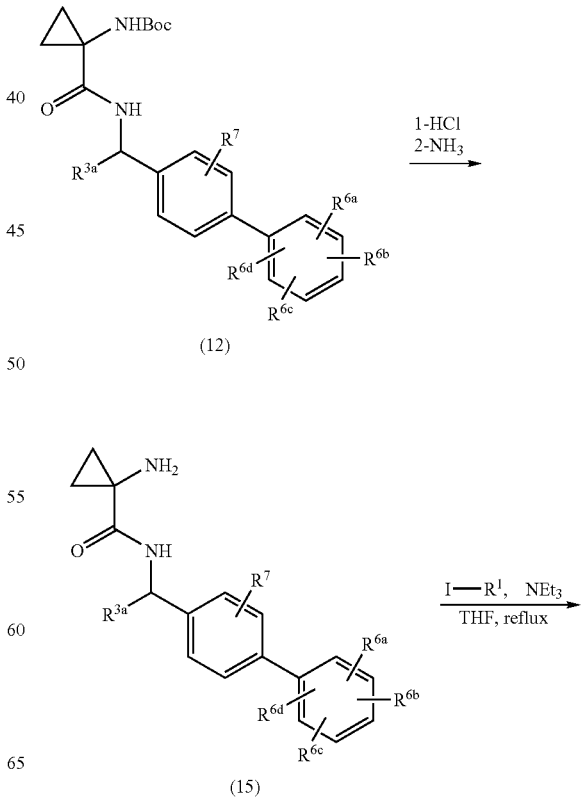

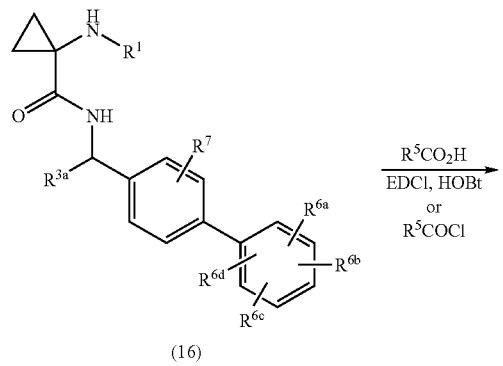

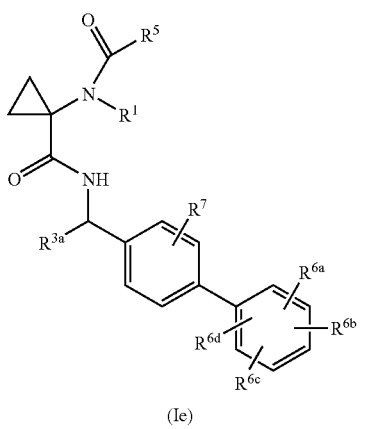

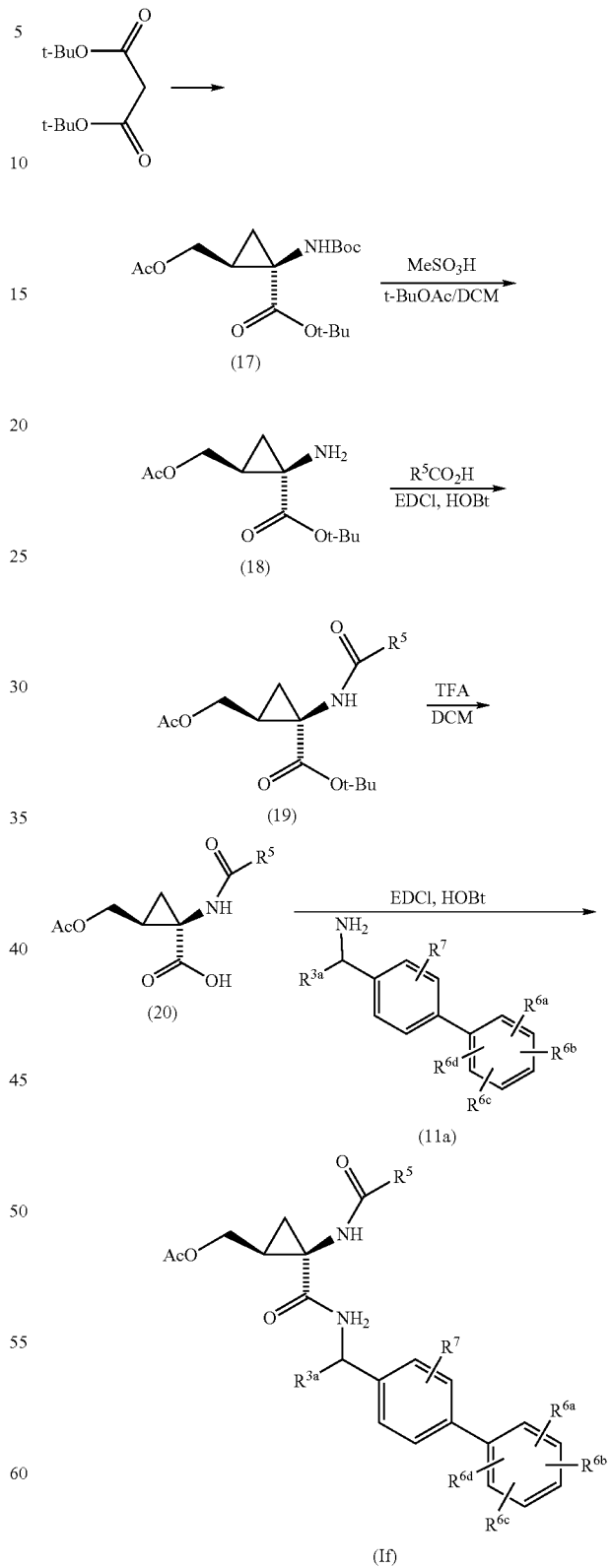

Alternatively, as illustrated in Scheme 4, according to known procedures (K. Burgess et al., *J. Org. Chem.*, 57:5931-5936 (1992)), di-tert-butyl malonate is elaborated to derivative (17). The N-Boc group is removed using methane sulfonic acid according to L. S. Lin et al. *Tetrahedron Lett.*, 41:7013-7016(2000) to give amine (18). This amine is allowed to react with a carboxylic acid or carboxylic acid equivalent under appropriate peptide coupling conditions to yield (19). The tert-butyl ester is then cleaved with an acid, like TFA, in an appropriate solvent, like DCM, to provide acid (20). Benzylic amine (11a), having been prepared according to Scheme 2, is then coupled with the acid (20) using an appropriate set of peptide coupling reagents, like EDCI/HOBt, to produce the title compound (If). Further elaboration of (If) to additional compounds of formula I may be accomplished using procedures well known to those skilled in the art. For example, the acetyl group may be removed by hydrolysis to provide the corresponding alcohol; the alcohol may be converted to the corresponding sulfonate by treatment with sulfonyl chloride, and the sulfonate may be converted to the corresponding halide by treatment with a source of the halide. These and other functional transformations to provide compounds of formula I are described in typical organic chemistry textbooks such as March's Advanced Organic Chemistry: Reactions, Mechanisms, and Structure, 5th Ed., John Wiley & Sons, 2000.

Alternately, as illustrated in Scheme 5, according to known procedures (K. Burgess et al., *J. Org. Chem.*, 57:5931-5936(1992)), di-tert-butyl malonate is elaborated to derivative (21). The N-Boc group is removed using an acid, like TFA, in an appropriate solvent, like DCM. This amine is allowed to react with a carboxylic acid or carboxylic acid equivalent under appropriate peptide coupling conditions, like EDCI/HOBt/NEt₃ to yield (22). Benzylic amine (11a), having been prepared according to Scheme 2, is then allowed to open the lactone (22) in an appropriate aprotic solvent, like DMF, at a temperature between 20 and 100° C., to produce the title compound (Ig). Further elaboration of (Ig) to additional title compounds may be accomplished using procedures well known to those skilled in the art as previously discussed.

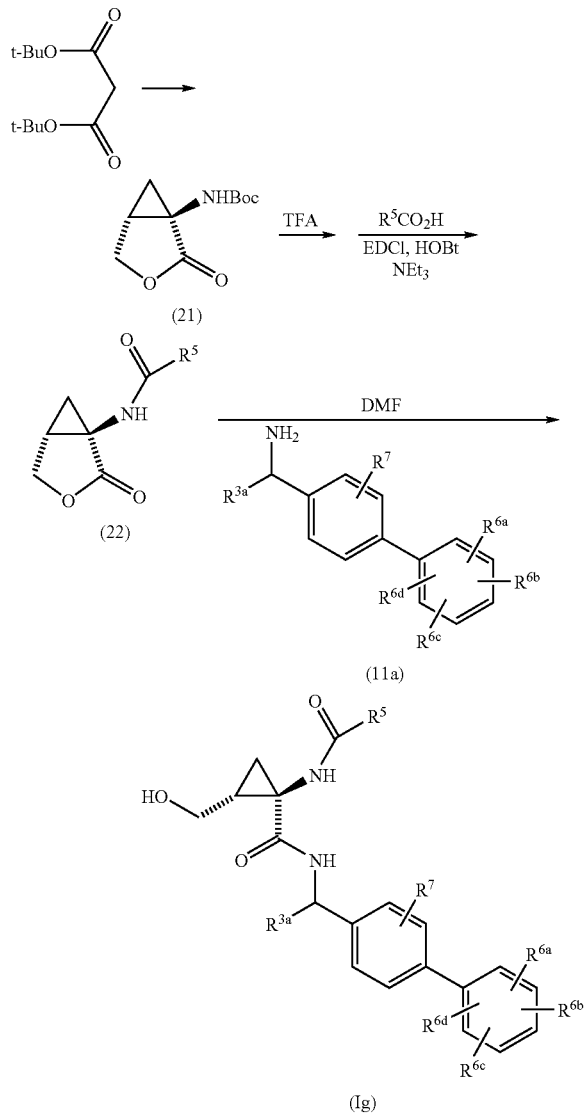

(Ig)

REFERENCE EXAMPLE 1

Preparation of (1R)-1-(3,3'-difluoro-2'-hydroxy-1,1'-biphenyl-4-yl)ethanaminium bromide. To a solution of (1R)-1-(4-bromo-2-fluorophenyl)ethanaminium chloride (14.24 g, 55.95 mmol) in CH₂Cl₂ (300 mL) at 0° C. was added di(tert-butyl) dicarbonate (17.98 g, 82.40 mmol) and triethylamine (8.256 g, 81.58 mmol). The solution was washed with water and brine, dried over Na2SO4, filtered and concentrated under reduced pressure to provide tert-butyl (1R)-1-(4-bromo-2-fluorophenyl)ethylcarbamate as a white solid that gave proton NMR spectra consistent with theory.

A mixture of the above compound (26.42 g, 83.03 mmol), bis(pinacolato)diboron (31.63 g, 0.1246 mol), potassium acetate (24.45 g, 0.2491 mol), and [1,1'-bis(diphenylphosphino)ferrocene]palladium(II) dichloride (0.265 g, 0.362 mmol) in 80 mL DMSO was heated at 90° C. under N₂ for 3 hours. The mixture was then cooled to room temperature and partitioned between ethyl acetate and water. The organic extract was washed with water and brine, dried over Na₂SO₄, filtered and concentrated under reduced pressure. The residue was subjected to silica gel chromatography and eluted with 0-10% ethyl acetate in hexanes to provide tert-butyl(1R)-1-[2-fluoro-4-(4,4,5,5-tetramethyl-1,3,2-dioxaborolan-2-yl)phenyl]ethylcarbamate as a beige solid that gave proton NMR spectra consistent with theory.

The above compound (7.00 g, 19.164 mmol), tris(dibenzylideneacetone)-dipalladium(0) (1.755 g, 1.916 mmol), tricyclohexylphosphine (1.344 g, 4.791 mmol), and cesium carbonate (7.493 g, 22.997 mmol) were added to a flame-dried flask under argon. To this was added dioxane (50 mL) and subsequently 1-bromo-3-fluoro-2-methoxybenzene (4.912 g, 23.956 mmol). This suspension was heated at 85° C. for 12 hours. The reaction was filtered through celite and concentrated in vacuo. The residue was adsorbed onto silica gel and purified by flash chromatography eluting with 10% ethyl acetate in hexanes to yield tert-butyl(1R)-1-(3,3'-difluoro-2'-methoxy-1,1'-biphenyl-4-yl)ethylcarbamate. Low resolution mass spectrometry: (M+H⁺)=364.2.

The above compound (5.75 g, 15.822 mmol) was dissolved in CH₂Cl₂ and cooled to −78° C. To this solution was added boron tribromide as a 1M solution in CH₂Cl₂ (31.645 mL, 31.645 mmol) and then was allowed to warm to 25° C. After 16 hours the reaction was again cooled to −78° C. and quenched with methanol (500 mL) and concentrated under reduced pressure to yield the title compound. Low resolution mass spectrometry: (M+H⁺—NH₃)=233.2.

REFERENCE EXAMPLE 2

Preparation of 1-[(trifluoroacetyl)amino]cyclopropanecarboxylic acid. 1-Carboxycyclopropanaminium chloride (0.980 g, 7.124 mmol) was suspended in methanol (14 mL) and triethylamine (1.514 g, 14.960 mmol) was subsequently added. To this suspension was then added ethyl trifluoroacetate (1.113 g, 7.836 mmol) and allowed to stir at 25° C. After 16 hours, the reaction was quenched with 1N hydrochloric acid and extracted with ethyl acetate. The organic extract was dried with sodium sulfate, filtered and concentrated under reduced pressure to produce the title compound as a white solid. 1H NMR (400 MHz, (CD3)2SO) δ 12.76 (s, 1H), 9.94 (s, 1H), 1.38-1.44 (m, 2H), 1.08-1.14 (m, 2H).

REFERENCE EXAMPLE 3

Preparation of 1-[(pyrimidin-5-ylcarbonyl)amino]cyclopropanecarboxylic acid compound with chlorolithium (1:1). Triethylamine (7.026 g, 69.44 mmol) was added to a suspension of 1-(ethoxycarbonyl)cyclopropanaminium chloride (11.50 g, 69.44 mmol), pyrimidine-5-carboxylic acid (8.617 g, 69.44 mmol), EDC (13.312 g, 69.44 mmol), and HOAT (0.945 g, 69.44 mmol) in CH₂Cl₂ (125 mL) and allowed to stir for 16 hours. The reaction was adsorbed onto silica and purified by silica gel chromatography and eluted with ethyl acetate to yield ethyl 1-[(pyrimidin-5-ylcarbonyl)amino]-cyclopropanecarboxylate as a white solid. Low resolution mass spectrometry: (M+H⁺)=236.2.

To the above compound (13.50 g, 57.39 mmol) in CH$_3$CN/MeOH (1:1, 200 mL) was added 1N lithium hydroxide solution (60 mL, 60 mmol) and allowed to stir for 16 hours. The reaction was quenched by addition of 1N hydrochloric acid (60 mL, 60 mmol) and was concentrated under reduced pressure with heating to yield the title compound as a white. Low resolution mass spectrometry: (M+H$^+$)=208.1.

The following examples are provided to illustrate the invention without limiting the invention to the particulars of these examples. Compounds were named using: ACD/Name version 4.53 (Advanced Chemistry Development Inc. © 1994-2000). Address: 90 Adelaide Street West, Toronto, Ontario, M5H 3V9, Canada.

EXAMPLE 1

3,3'-Difluoro-4'-{[({1-[(pyrimidin-5-ylcarbonyl)amino]cyclopropyl}carbonyl)amino]methyl}-1,1'-biphenyl-2-yl trifluoromethanesulfonate

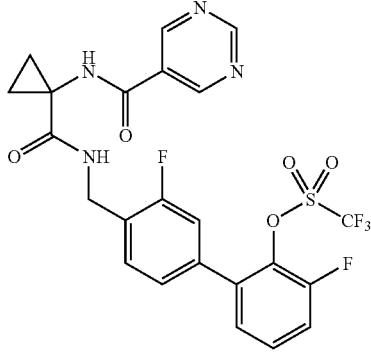

Triethylamine (1.036 g, 10.24 mmol) was added to a stirred solution of the compound of reference Example 3 (2.556 g, 10.24 mmol), (4-bromo-2-fluorophenyl)methanaminium chloride (2.463 g, 10.24 mmol), EDC (1.963 g, 10.24 mmol), and HOAT (0.418 g, 3.072 mmol) in CH$_2$Cl$_2$ (25 mL). After 1 h, the reaction was diluted with water and extracted with ethyl acetate. The organic extract was washed with water, dried over sodium sulfate, filtered and concentrated under reduced pressure to yield a yellow solid. This solid was purified by silica gel chromatography, eluting with 5% methanol/CH$_2$Cl$_2$ to yield N-(1-{[(4-bromo-2-fluorobenzyl)amino]carbonyl}cyclopropyl)pyrimidine-5-carboxamide as a white solid. Low resolution MS: (M+H$^+$)=393.03.

The above compound (0.050 g, 0.127 mmol), bis(pinacolato)diboron (0.039 g, 0.153 mmol), dichloro[1,1'-bis(diphenylphosphino)ferrocene]palladium (11) dichloromethane adduct (0.009 g, 0.013 mmol) and potassium acetate were combined in a flame-dried flask under argon. To these solids was added DMSO (1 mL) and the reaction was heated at 90° C. After 2 hours, the reaction was diluted with ethyl acetate, washed with water (3×), washed with brine (1×), washed with water again (1×), dried with sodium sulfate, filtered and concentrated to a solid under reduced pressure. This solid was purified using silica gel chromatography and eluted with 7% methanol/CH$_2$Cl$_2$ to give N-[1-({[2-fluoro-4-(4,4,5,5-tetramethyl-1,3,2-dioxaborolan-2-yl)benzyl]amino}carbonyl)cyclopropyl]pyrimidine-5-carboxamide as a solid. Low resolution mass spectrometry: (M+H$^+$)=441.2.

The above compound (1.200 g, 2.73 mmol), tetrakis(triphenylphosphine)palladium (0) (0.315 g, 0.273 mmol) and potassium phosphate (0.382 g, 1.80 mmol) were combined in a flame-dried test tube under argon. To these solids was added 1-bromo-3-fluoro-2-methoxybenzene (1.118 g, 545 mmol). This was suspended in DMSO (20 mL) and heated to 110° C. After 16 hours, the reaction was diluted with water and extracted with ethyl acetate. The organic extract was washed with water (3×), dried with sodium sulfate and concentrated to an oil. The oil was purified by silica gel chromatography, eluting with 5% methanol/CH$_2$Cl$_2$, to yield N-[1-({[(3,3'-difluoro-2'-methoxy-1,1'-biphenyl-4-yl)methyl]amino}-carbonyl)cyclopropyl]pyrimidine-5-carboxamide as a solid. Low resolution MS: (M+H$^+$)=439.2.

To a solution of the above compound (0.575 g, 1.311 mmol) in CH$_2$Cl$_2$ (2 mL) at −78° C. was added a 1M solution of boron tribromide in CH$_2$Cl$_2$ (1.971 g, 7.87 mmol) and allowed warm to room temperature. After 48 hours, the reaction was cooled to 0C, quenched with methanol and concentrated to a solid under reduced pressure. This solid was purified by reverse phase chromatography using a gradient from 95/5H$_2$O/CH$_3$CN to 5/95H$_2$O/CH$_3$CN. The product was lyophilized to yield N-[1-({[(3,3'-difluoro-2'-hydroxy-1,1'-biphenyl-4-yl)methyl]amino}carbonyl)cyclopropyl]pyrimidine-5-carboxamide as a solid. Low resolution mass spectrometry: (M+H$^+$)=425.2.

To a stirred solution of the above compound (0.090 g, 0.212 mmol) and triethylamine (0.164 g, 1.272 mmol) in CH$_2$Cl$_2$ (2 mL) at −78° C. was added tifluoromethanesulfonic anhydride (0.120 g, 0.424 mmol). This was allowed to warm to room temperature. After 2 hours the reaction was diluted with CH$_2$Cl$_2$ and poured into water. The organic extract was isolated, dried with sodium sulfate, filtered and concentrated under reduced pressure to yield the title compound as a solid. Low resolution MS: (M+H$^+$)=557.1.

EXAMPLE 2

3,3'-Difluoro-4'-{(1R)-1-[({1-[(trifluoroacetyl)amino]cyclopropyl}carbonyl)amino]ethyl}-1,1'-biphenyl-2-yl trifluoromethanesulfonate

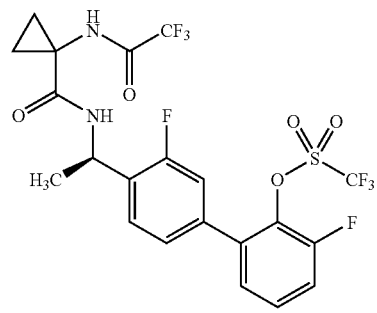

The compound of reference Example 1 (0.838 g, 2.537 mmol), 1-[(trifluoroacetyl)amino]-cyclopropanecarboxylic acid (0.500 g, 2.537 mmol), EDC (0.486 g, 2.537 mmol), and HOAT (0.345 g, 2.537 mmol) were combined. To this was added a 1:1 ratio of CH$_3$CN/CH$_2$Cl$_2$ (25 mL) and then triethylamine (0.257 g, 2.537 mmol). After 16 hours, the reaction was concentrated in vacuo to a solid. This was purified by silica gel chromatography eluting with 7% methanol/CH$_2$Cl$_2$ to isolate N-[(1R)-1-(3,3'-difluoro-2'-hydroxy-1,1'-biphenyl-4-yl)ethyl]-1-[(trifluoroacetyl)amino]cyclopropanecarboxamide. High resolution mass spectrometry: C$_{20}$H$_{17}$F$_5$N$_2$O$_3$ requires: 429.1232, found: 429.1187.

The above compound (0.100 g, 0.233 mmol) and triethylamine (0.060 g, 0.466 mmol) were dissolved in CH$_2$Cl$_2$ (2 mL) and cooled to −78 C. To this solution was added trifluoromethanesulfonic anhydride (0.072 g, 0.257 mmol). After 30 minutes the reaction was quenched with a saturated bicarbonate solution and warmed to 25 C. Extracted with $CH_2Cl_2$, dried extract over $Na_2SO_4$, filtered and concentrated under reduced pressure to obtain a solid. This solid was purified by silica gel chromatography and eluted with 5% methanol/$CH_2Cl_2$ to afford the title compound. High resolution mass spectrometry: $C_{21}H_{16}F_8N_2O_5S$ requires: 561.0725, found: 561.0729. $^1$H NMR (400 MHz, $(CD_3)_2SO$) δ 9.80 (s, 1H), 8.30 (d, J=7.4 Hz, 1H), 7.58-7.68 (m, 2H), 7.44-7.55 (m, 2H), 7.32-7.42 (m, 2H), 5.24 (qn, J=7.4 Hz, 1H), 1.41 (d, J=7.4 Hz, 3H), 1.30-1.38 (m, 2H), 0.92-1.08 (m, 2H).

EXAMPLE 3

3,3'-Difluoro-4'-{(1R)-1-{[(1-{[(trifluoromethyl)sulfonyl]amino}cyclopropyl)carbonyl]amino}ethyl)-1,1'-biphenyl-2-yl trifluoromethanesulfonate

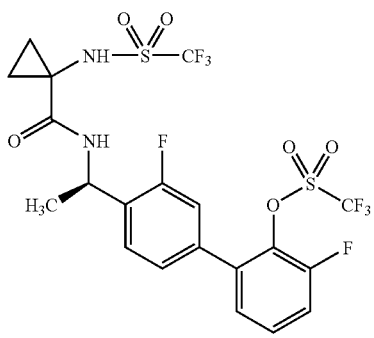

N-[(1R)-1-(3,3'-difluoro-2'-hydroxy-1,1'-biphenyl-4-yl)ethyl]-1-[(trifluoroacetyl)amino]-cyclopropanecarboxamide (1.930 g, 4.51 mmol) and triethylamine (2.912 g, 22.53 mmol) were dissolved in $CH_2Cl_2$ (20 mL) and cooled to −78 C. To this solution was added trifluoromethanesulfonic anhydride (2.225 g, 7.885 mmol). After 30 minutes the reaction was quenched with a saturated bicarbonate solution and warmed at 25° C. Extracted with $CH_2Cl_2$, dried extract over $Na_2SO_4$, filtered and concentrated under reduced pressure to obtain a solid. This solid was suspended in 6N hydrochloric acid (10 mL) and heated to 90° C. After 1.5 hours the reaction was poured into a saturated aqueous bicarbonate solution that was subsequently extracted with ethyl acetate. The organic extract was dried with sodium sulfate, filtered and concentrated to a solid under reduced vacuum. This solid was then purified by reverse phase chromatography utilizing a gradient from 95/5$H_2O$/$CH_3CN$ to 5/95$H_2O$/$CH_3CN$. The product was lyophilized yielding the title compound as a solid. High resolution mass spectrometry:

$C_{20}H_{16}F_8N_2O_6S_2$ requires: 597.0395, found: 597.0392. $^1$H NMR (400 MHz, $(CD_3)_2SO$) δ 10.10 (s, 1H), 7.81 (d, J=7.3 Hz, 1H), 7.58-7.68 (m, 2H), 7.40-7.52 (m, 2H), 7.33-7.43 (m, 2H), 5.21 (qn, J=7.3 Hz, 1H), 1.44-1.49 (m, 2H), 1.41 (d, J=7.3 Hz, 3H), 1.17-1.24 (m, 2H).

EXAMPLE 4

3,3'-Difluoro-4'-{(1R)-1-[({1-[(trifluoroacetyl)amino]cyclopropyl}carbonyl)amino]ethyl}-1,1'-biphenyl-2-yl methanesulfonate

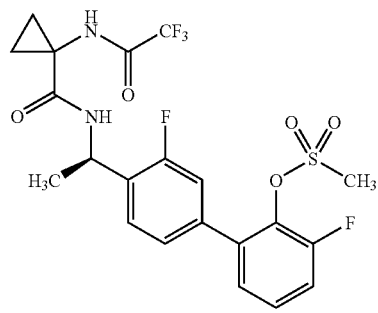

N-[(1R)-1-(3,3'-difluoro-2'-hydroxy-1,1'-biphenyl-4-yl)ethyl]-1-[(trifluoroacetyl)amino]cyclopropanecarboxamide (0.040 g, 0.093 mmol) and triethylamine (0.019 g, 0.187 mmol) were dissolved in $CH_2Cl_2$ (2 mL) and cooled to −78 C. To this solution was added methanesulfonyl chloride (0.012 g, 0.103 mmol) and the reaction was allowed to stir for 16 hours. The reaction was concentrated under reduced pressure, diluted with methanol and purified by reverse phase chromatography using a gradient from 95/5$H_2O$/$CH_3CN$ to 5/95$H_2O$/$CH_3CN$. Product was lyophilized to yield the title compound as a solid. High resolution mass spectrometry: $C_{21}H_{19}F_5N_2O_5S$ requires: 507.1076, found: 507.1002. $^1$H NMR (400 MHz, $(CD_3)_2SO$) δ 9.79 (s, 1H), 8.30 (d, J=7.5 Hz, 1H), 7.44-7.54 (m, 3H), 7.30-7.39 (m, 3H), 5.23 (qn, J=7.5 Hz, 1H), 2.99 (s, 1H), 1.4.2 (d, J=7.5 Hz, 3H), 1.32-1.38 (m, 2H), 0.92-1.06 (m, 2H).

EXAMPLE 5

5-Chloro-3,3'-difluoro-4'-{(1R)-1-[({1-[(trifluoroacetyl)amino]cyclopropyl}carbonyl)amino]ethyl}-1,1'-biphenyl-2-yl trifluoromethanesulfonate

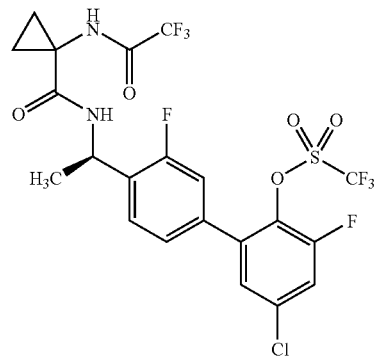

To a solution of N-[(1R)-1-(3,3'-difluoro-2'-hydroxy-1,1'-biphenyl-4-yl)ethyl]-1-[(trifluoroacetyl)amino]cyclopropanecarboxamide (125 mg, 0.292 mmol) in acetic acid (1 ml) was added N-chlorosuccinimide (39 mg, 0.292 mmol) and the solution was heated to 90 C for 2 h. After this time, the mixture was concentrated in vacuo and purified by column chromatography eluting with a 0-10% EtOAc/

CH₂Cl₂ gradient to give N-[(1R)-1-(5'-chloro-3,3'-difluoro-2'-hydroxy-1,1'-biphenyl-4-yl)ethyl]-1-[(trifluoroacetyl)amino]cyclopropanecarboxamide. Low resolution mass spectrometry: (M+H⁺)=462.9. ¹H NMR (400 MHz, CDCl₃) δ 7.26-7.34 (m, 3H), 7.12 (dd, 1H, J=9.9 and 2.4 Hz), 7.08 (s, 1H), 6.98 (s, 1H), 6.59 (d, 1H, J=8.6 Hz), 5.38-5.51 (br, 1H), 5.23 (quin, 1H, J=7.2 Hz), 1.55-1.70 (m, 2H), 1.52 (d, 3H, 7.2 Hz) and 1.08-1.21 (m, 2H) ppm.

In an analogous manner to Example 2 using N-[(1R)-1-(5'-chloro-3,3'-difluoro-2'-hydroxy-1,1'-biphenyl-4-yl)ethyl]-1-[(trifluoroacetyl)amino]cyclopropanecarboxamide, the title compound was obtained as a solid. High resolution mass spectrometry: ¹H NMR (400 MHz, CD₃CN) δ 8.10 (br s, 1H), 7.52 (dd, 1H, J=2.5 and 9.7 Hz), 7.46 (dd, 1H, J=5 and 9.7 Hz), 7.46 (s, 1H), 7.31 (dd, 1H, J=1.7 and 8.0 Hz), 7.26 (dd, 1H, J=1.7 and 11.3 Hz), 7.18 (d, 1H, J=9.2 Hz), 5.26 (quin, 1H, J=7.0 Hz), 1.46 (d, 3H, J=7.0 Hz), 1.34-1.45 (m, 2H) and 1.01-1.16 (m, 2H) ppm.

The following compounds were prepared in an analogous manner as that dexcribed in Example 4.

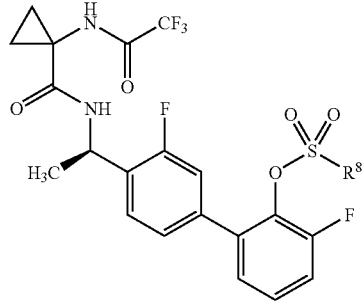

| Ex. | R⁸ (reagent) | Compound Name; MS; ¹H NMR (400 MHz, (CD₃)₂SO) |
|---|---|---|
| 6 | Ethyl (ethanesulfonyl chloride) | 3,3'-Difluoro-4'-{(1R)-1-[({1-[(trifluoroacetyl)-amino]cyclopropyl}carbonyl)-amino]ethyl}-1,1'-biphenyl-2-yl ethanesulfonate. HRMS 521.1161 δ 10.12 (s, 0.28H), 9.79 (s, 0.72H), 8.96 (s, 0.28H), 8.30 (d, J = 7 Hz, 0.72H) 7.43-7.54 (m, 3H), 7.26-7.37 (m, 3H), 5.14-5.26 (m, 1H), 2.96-3.08 (n 2H), 1.42 (d, J =7 Hz, 3H), 1.20-1.38 (m, 2H), 0.84-1.10 (m. 5H) |
| 7 | n-propyl (propanesulfonyl chloride) | 3,3'-difluoro-4'-{(1R)-1-[({1-[(trifluoroacetyl)amino]cyclopropyl}carbonyl)-amino]ethyl}- 1,1'-biphenyl-2-yl propane-1-sulfonate. HRMS 535.1299 δ 10.14 (s, 0.23H), 9.80 (s, 0.77H), 8.98 (s, 0.24H), 8.32 (d, J = 7.8 Hz, 0.76H), 7.45-7.55 (m, 3H), 7.27-7.38 (m, 3H), 5.16-5.30 (m, 1H), 2.90-3.02 (m, 2H), 1.48-1.60 (m, 2H), 1.22-1.46 (m, 5H), 0.88-1.08 (m, 2H), 0.74-0.82 (m, 3H) |
| 8 | Isopropyl (propane-2-sulfonyl chloride) | 3,3'-difluoro4'-{(1R)-1-[({1-[(trifluoroacetyl)amino]cyclopropyl}carbonyl)-amino]ethyl }-1,1'-biphenyl-2-yl propane-2-sulfonate. HRMS 535.1307 δ 10.13 (s, 0.13H), 9.79 (s, 0.87H), 8.96 (s, 0.14H), 8.31 (d, J = 7.5 Hz, 0.86H), 7.40-7.56 (m, 3H), 7.24-7.36 (m, 3H), 5.21 (qn, J = 7.5 Hz, 1H), 2.90-3.00 (sp, J = 6.7 Hz, 1H), 1.41 (d, J = 7.5 Hz, 3H), 1.30-1.70 (m, 2H) 1.15 (d, J = 6.7 Hz, 6H), 0.90-1.08 (m, 2H) |
| 9 | Phenyl (benzenesulfonyl chloride) | 3,3'-difluoro-4'-{(1R)-1-[({1-[(trifluoroacetyl)amino]cyclopropyl}carbonyl)-amino]ethyl}-1,1'-biphenyl-2-yl benzenesulfonate. HRMS 569.1140 δ 10.16 (s, 0.37H), 9.83 (s, 0.63H), 9.00 (s, 0.38H), 8.29 (d, J = 8.2 Hz, 0.62H), 7.60-7.66 (m, 1H), 7.42-7.48 (m, 2H), 7.34-7.40 (m, 4H), 7.20-7.30 (m, 2H), 6.94-7.02 (m, 1H), 6.78-6.84 (m, 1H), 5.10-5.22 (m, 1H), 1.28-1.48 (m, 5H), 0.90-1.12 (m, 2H). |
| 10 | Benzyl (phenylmethane-sulfonyl chloride) | 3,3'-difluoro-4'-{(1R)-1-[({1-[(trifluoroacetyl)amino]cyclopropyl}carbonyl)-aminoethyl}-1,1'-biphenyl-2-yl phenylmethanesulfonate. HRMS 583.1299 δ 10.11 (s, 0.23H), 9.78 (s, 0.77H), 8.95 (s, 0.24H), 8.30 (d, J = 8.0 Hz, 0.76H), 7.44-7.54 (m, 3H), 7.34-7.40 (m, 4H), 7.28-7.34 (m, 4H), 5.14-5.26 (m, 1H), 4.44-4.54 (m, 2H), 1.35-1.42 (m, 3H), 1.14-1.34 (m, 2H), 0.80-1.08 (m, 2H) |
| 11 | —N(CH₃)₂ (dimethylsulfamoyl chloride) | 3,3'-difluoro-4'-{(1R)-1-[({1-[(trifluoroacetyl)amino]cyclopropyl}carbonyl)-amino]ethyl}-1,1'-biphenyl-2-yl dimethylsulfainate. HRMS 536.1260 δ 10.12 (s, 0.76H), 9.78 (s, 0.24H), 8.96 (s, 0.76H), 8.30 (d, J = 7.2 Hz, 0.24H), 7.40-7.55 (m, 3H), 7.27-7.38 (m, 3H), 5.12-5.24 (m, 1H), 2.42-2.48 (m, 6H), 1.32-1.44 (m, 5H), 0.82-0.98 (m, 2H) |
| 12 | —CH₂CF₃ (2,2,2-trifluoro-ethanesulfonyl chloride) | 3,3'-difluoro4'-{(1R)-1-[({1-[(trifluoroacetyl)amino]cyclopropyl}carbonyl)-amino]ethyl}-1,1'-biphenyl-2-yl 2,2,2-trifluoroethanesulfonate LRMS (M+H+) 575.1 δ 9.89 (s, 1H), 8.32 (d, J = 7.2 Hz, 1H), 7.43-7.52 (m, 2H), 7.33-7.40 (m, 1H), 7.21-7.32 (m, 3H), 5.33 (qn, J = 7.2 Hz, 1H), 4.21 (q, J = 9.1 Hz, 2H), 1.46-1.56 (m, 5H), 1.02-1.16(m, 2H). |
| 13 | 4-(acetylamino)-phenyl (4-(acetylamino)-benzenesulfonyl chloride) | 3,3'-difluoro-4'-{(1R)-1-[({1-[(trifluoroacetyl)amino]cyclopropyl}carbonyl)-amino]ethyl}biphenyl-2-yl 4-acetylbenzenesulfonate. MH+ 626.3 |

EXAMPLE 14

3-Chloro-3'-fluoro-4'-{(1R)-1-[({1-[(trifluoroacetyl)amino]cyclopropyl}carbonyl)amino]ethyl}-1,1'-biphenyl-2-yl trifluoromethanesulfonate

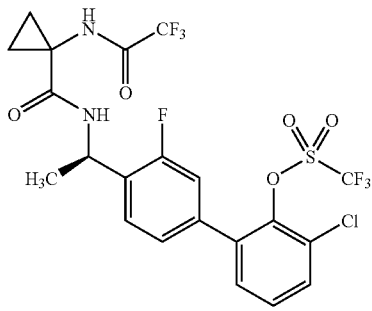

Tert-butyl(1R)-1-(4-bromo-2-fluorophenyl)ethylcarbamate (10.04 g, 31.55 mmol) was dissolved in ethyl acetate and treated with hydrochloric acid gas. A white solid precipitated and the suspension was concentrated under reduced pressure to yield (1R)-1-(4-bromo-2-fluorophenyl)ethanaminium chloride as a white solid that was used without further purification. Low resolution mass spectrometry: (M+H+−NH$_3$)=201.1.

(1R)-1-(4-Bromo-2-fluorophenyl)ethanaminium chloride (16.50 g, 64.83 mmol), 1-[(trifluoroacetyl)amino]cyclopropanecarboxylic acid (12.78 g, 64.83 mmol), EDC (12.43 g, 64.83 mmol), and HOAT (4.41 g, 32.41 mmol) were dissolved in dimethylformamide (100 mL). To this solution was added triethylamine (6.56 g, 64.83 mmol). After 6 hours, the reaction was diluted with water and extracted with ethyl acetate. The organic extract was washed with water, dried over sodium sulfate, filtered and concentrated under reduced pressure to yield a solid. This solid was purified by silica gel chromatography and eluted with 5% methanol/CH$_2$Cl$_2$ to yield N-[(1R)-1-(4-bromo-2-fluorophenyl)ethyl]-1-[(trifluoroacetyl)amino]cyclopropanecarboxamide as a white solid. Low resolution mass spectrometry: (M+H+)=399.0.

A mixture of the above compound (6.0 g, 15.11 mmol), bis(pinacolato)diboron (4.60 g, 18.13 mmol), potassium acetate (4.45 g, 45.32 mol), and [1,1'-bis(diphenylphosphino)ferrocene]-palladium(II) dichloride (1.234 g, 1.511 mmol) in DMSO (30 ml) was heated at 90° C. under N$_2$ for 1 hour. The mixture was then cooled to room temperature and partitioned between ethyl acetate and water. The organic extract was washed with water and brine, dried over Na$_2$SO$_4$, filtered and concentrated under reduced pressure. The residue was purified by silica gel chromatography eluting with a 0-100% EtOAc with CH$_2$Cl$_2$ to provide N-{(1R)-1-[2-fluoro-4-(4,4,5,5-tetramethyl-1,3,2-dioxaborolan-2-yl)phenyl]-ethyl}-1-[(trifluoroacetyl)amino]cyclopropanecarboxamide as a brown solid. Low resolution mass spectrometry: (M+H+)=445.1. $^1$H NMR (400 MHz, CDCl$_3$) δ 7.53 (d, 1H, 7.5 Hz), 7.46 (d, 1H, 11.5 Hz), 7.23 (t, 1H, 7.5 Hz), 6.90 (br s, 1H), 6.61 (br d, 1H), 5.20 (qn, 1H), 1-53-1.67 (m, 2H), 1.48 (d, 3H, 7.0 Hz) and 1.06-1.18 (m, 2H)ppm.

The above compound (2.00 g, 4.50 mmol) was dissolved in methanol (5 mL). To this solution was added concentrated hydrochloric acid (5 mL). After 3 hours the reaction was diluted with DMF and purified by reverse phase chromatography using a gradient from 95/5H$_2$O/CH$_3$CN to 5/95H$_2$O/CH$_3$CN. The product was lyophilized to yield 3-fluoro-4-{(1R)-1-[({1-[(trifluoroacetyl)amino]cyclopropyl}carbonyl)amino]ethyl}phenylboronic acid as a white solid. Low resolution mass spectrometry: (M+H+) =363.1

Triethylamine (2.87 g, 28.36 mmol) was added to a solution of 3-chlorobenzene-1,2-diol (1.025 g, 7.09 mmol) in CH$_2$Cl$_2$ (20 mL). This was cooled to −78° C. and trifluoromethanesulfonic anhydride (4.00 g, 14.18 mmol) was added and the reaction was allowed to warm to room temperature. After 1 hour, the reaction was quenched with a saturated aqueous solution of sodium bicarbonate. Extracted with CH$_2$Cl$_2$. The organic extract was dried with sodium sulfate, filtered and concentrated under reduced pressure to an oil that was subsequently adsorbed onto silica gel. This was purified by flash chromatography, eluting with 10% ethyl acetate/hexanes to yield 2-chloro-6-{[(trifluoromethyl)sulfonyl]oxy}phenyl trifluoromethanesulfonate as an oil. $^1$H NMR (400 MHz, (CD$_3$)$_2$SO) δ 7.98 (d, J=8.4 Hz, 1H), 7.90 (d, J=8.4 Hz, 1H), 7.76 (t, J=8.4 Hz, 1H).

3-Fluoro-4-{(1R)-1-[({1-[(trifluoroacetyl)amino]cyclopropyl}carbonyl)amino]ethyl}-phenylboronic acid (0.050 g, 0.138 mmol), tetrakis(triphenylphosphine)palladium (0) (0.016 g, 0.014 mmol), and potassium phosphate (0.035 g, 0.166 mmol) were added to a flame-dried flask under argon. 2-Chloro-6-{[(trifluoromethyl)sulfonyl]oxy}phenyl trifluoromethanesulfonate (0.068 g, 1.66 mmol) as a solution in dioxane (0.33M) was added to the solids and heated to 90° C. After 3 hours the reaction was diluted with methanol, filtered and purified by reverse phase chromatography using a gradient from 95/5H$_2$O/CH$_3$CN to 5/95H$_2$O/CH$_3$CN. The product was lyophilized to yield the title compound as a solid.

$^1$H NMR (400 MHz, (CD$_3$)$_2$SO) δ 9.80 (s, 1H), 8.31 (d, J=7.5 Hz, 1H), 7.76-7.83 (m, 1H), 7.56-7.63 (m, 2H), 7.50 (t, J=8 Hz, 1H), 7.38 (dd, J=10.6 Hz, J=1.5 Hz, 1H), 7.33 (dd, J=8 Hz, J=1.5 Hz, 1H), 5.23 (qn, J=7.5 Hz, 1H), 1.41 (d, J=7.5 Hz, 3H), 1.29-1.39 (m, 2H), 0.92-1.07 (m, 2H).

EXAMPLE 15

3'-Fluoro-4'-{(1R)-1-[({1-[(trifluoroacetyl)amino]cyclopropyl}carbonyl)amino]ethyl}-2-{[(trifluoromethyl)sulfonyl]oxy}-1,1'-biphenyl-3-yl trifluoromethanesulfonate

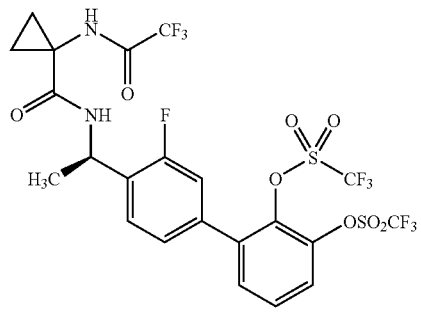

3-Fluoro-4-{-(1R)-1-[({1-[(trifluoroacetyl)amino]cyclopropyl}carbonyl)amino]ethyl}-phenylboronic acid (0.050 g, 0.138 mmol), tris(dibenzylideneacetone)dipalladium (0) (0.013 g, 0.014 mmol), and cesium carbonate (0.054 g, 0.166 mmol) were added to a flame-dried flask under argon. 2-chloro-6-{[(trifluoromethyl)sulfonyl]oxy}phenyl trifluoromethanesulfonate (0.068 g, 1.66 mmol) as a solution in dioxane (0.33M) and tri-tert-butyl phosphine (0.007 g, 0.035 mmol) as a solution in dioxane (1.65M) were added to the solids and heated at 85° C. After 1.5 hours the reaction was diluted with methanol, filtered and purified by reverse phase chromatography using a gradient from 95/5H$_2$O/CH$_3$CN to 5/95H$_2$O/CH$_3$CN. The product was lyophilized to yield the title compound as a solid. High resolution mass spectrometry: C$_{22}$H$_{16}$F$_{10}$N$_2$O$_8$S$_2$ requires: 691.0261, found: 691.0275. $^1$H NMR (400 MHz, (CD$_3$)$_2$SO) δ 9.80 (s, 1H), 8.32 (d, J=7.4 Hz, 1H), 7.86-7.92 (m, 1H), 7.76-7.81 (m, 2H), 7.53 (t, J=7.9 Hz, 1H), 7.37 (dd, J=11 Hz, J=1.7 Hz, 1H), 7.33 (dd, J=7.9 Hz, J=1.7 Hz, 1H), 5.24 (qn, J=7.4 Hz, 1H), 1.41 (d, J=7.4 Hz, 3H), 1.30-1.37 (m, 2H), 0.92-1.08 (m, 2H).

EXAMPLE 16

(1-(3-Fluoro-4-{(1R)-1-[({1 [(trifluoroacetyl)amino] cyclopropyl}carbonyl)amino]ethyl}phenyl)-2-naphthyl trifluoromethanesulfonate.

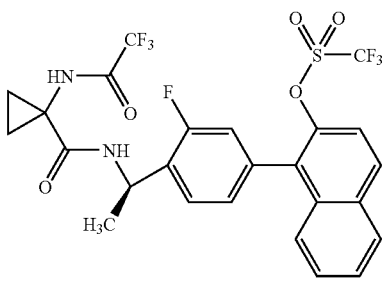

1-Bromo-2-naphthol (2.0 g, 8.97 mmol) was dissolved in THF (20 mL), and the solution was cooled to 0 deg in an ice bath. NaH was added thereto (60% dispersion of in mineral oil, 430 mg 10.8 mmol), followed by MeI (1.2 mL, 19.6 mmol) as bubbling subsided. The reaction mixture was heated to reflux overnight, cooled to room temperature, and water added dropwise thereto until bubbling subsided. The reaction mixture was diluted with EtOAc, and the organic layer was washed once each with water and brine, dried over sodium sulfate, filtered, and concentrated under reduced pressure. The residue was purified by silica gel chromatography eluting with 10% to 50% EtOAc/hexanes to afford 1-bromo-2-methoxynaphthalene as a solid. LC/MS (ES MS, M+H$^+$ found: 238) and proton NMR (400 MHz, CDCl$_3$) δ 4.04 (s, 3H), 7.28 (d, J=9 Hz, 1H), 7.42 (t, J=7 Hz, 1H), 7.58 (t, J=6.8 Hz, 1H), 7.8 (dd, J=9 Hz, 2H), 8.2 (d, J=8.6 Hz, 1H).

N-{(1R)-1-[2-fluoro-4-(4,4,5,5-tetramethyl-1,3,2-dioxaborolan-2-yl)phenyl]ethyl}-1-[(trifluoroacetyl)amino]cyclopropanecarboxamide, (1 g, 2.25 mmol), 1-bromo-2-methoxynaphthalene (534 mg (2.25 mmol), cesium carbonate (1.47 g 4.5 mmol), and bis(tri-t-butylphosphine) palladium (0) (6 mg 0.1 mmol) were stirred in anhydrous dioxane (4 mL) at 90 C overnight in a sealed tube. The reaction was cooled to room temperature and diluted with EtOAc, washed once each with water and brine. The organic layers were dried over sodium sulfate, filtered, and concentrated under reduced pressure. The residue was purified by silica gel chromatography eluting with 0% to 50% EtOAc/hex. To afford N-{(1R)-1-[2-fluoro-4-(2-methoxy-1-naphthyl)phenyl]ethyl}-1-[(trifluoroacetyl)amino]cyclopropanecarboxamide LC/MS (ES MS, M+H$^+$ found: 475) and proton NMR (400 MHz, CDCl$_3$) δ 1.2 (m, J=2.4 Hz, 2H), 1.58 (d, J=6.8 Hz, 3H), 1.7 (m, J=2.9 Hz, 2H), 3.86 (s, 3H), 5.33 (q, J=7.2 Hz, 1H), 6.64 (d, J=8.8 Hz, 1H), 6.84 (s, 1H), 7.08 to 7.19 (m, 3H), 7.34 (m, 3H), 7.47 (m, J=4.5 Hz, 1H), 7.81 (m, J=5 Hz, 1H), 7.9 (d, J=9 Hz, 1H).

The above compound (800 mg (1.7 mmol) was dissolved in DCM (5 ml). The solution was cooled to −78 C and BBr$_3$ (3.39 ml of a 1.0 M solution in DCM) was added dropwise, and stirring continued for 16 hours. The reaction was concentrated under reduced pressure. MeOH (5 mL) was added and the solvent was removed under vacuum. The residue was purified by silica gel chromatography eluting with 5% to 75% EtOAc/hex to afford N-{(1R)-1-[2-fluoro-4-(2-hydroxy-1-naphthyl)phenyl]ethyl}-1-[(trifluoroacetyl) amino]cyclopropanecarboxamide. LC/MS (ES MS, M+H$^+$ found: 461) and proton NMR (400 MHz, CDCl$_3$) δ 1.17 (m, 2H), 1.58 to 1.7 (m, 5H), 5.09 (s, 1H), 5.33 (q, J=8.1 Hz, 1H), 6.61 (b, 1H), 6.88 (s, 1H), 7.02 to 7.2 (m, 2H), 7.3 to 7.4 (m, 3H), 7.44 to 7.48 (t, J=7.7 Hz, 2H), 7.81 (d, J=9.1 Hz, 2H).

The above compound (50 mg 0.109 mmol) was dissolved in 2 ml of DCM and TEA (0.02 mL (0.141 mmol) was added. The reaction mixture was cooled to −78 C, and trifluoromethanesulfonic anhydride (0.028 mL 0.163 mmol) was added. After 10 minutes the reaction was warmed to room temperature and quenched with saturated sodium bicarbonate. The organic layer was separated and dried over sodium sulfate and concentrated under reduced pressure. The residue was purified by silica gel chromatography eluting with 5% to 70% EtOAc/hex to afford the title compound. LC/MS (ES MS, M+H$^+$ found: 593) and proton NMR (400 MHz, CDCl$_3$) δ 1.18 (m, 2H), 1.60 (d, J=6.8 Hz, 3H), 1.69 (m, 2H), 5.3 (q, J=7.1 Hz, 1H), 6.6 (b, 1H), 6.87 (d, J=11 Hz, 1H), 7.1 to 7.2 (m, 2H), 7.3 to 7.69 (m, 5H), 7.96 (t, J=8.5 Hz, 2H).

EXAMPLE 17

N-(1-{[((1R)-1-(3,3'-Difluoro-2'-[methyl(methylsulfonyl)amino]-1,1'-biphenyl-4-yl )ethyl)amino]carbonyl}cyclopropyl)pyrimidine-5-carboxamide

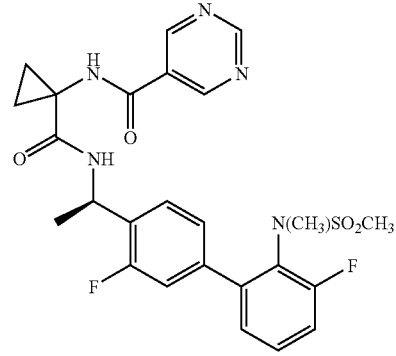

To a solution of 2-bromo-6-fluoroaniline (500 mg, 2.631 mmol) in pyridine (2 ml) was added methanesulfonic anhydride (1.35 g, 7.78 mmol) and the mixture was heated to 70 C for 3 hours. This solution was treated with 1.0N HCl to pH=1 and extracted with CH$_2$Cl$_2$ (2×40 ml). The combined organic extracts were washed with 1.0N HCl (20 ml), dried over MgSO$_4$, filtered and concentrated in vacuo to provide the bis mesylated product. This material was dissolved in methanol (20 ml) and treated with 1.0N NaOH (10 ml) for 45 minutes. After this time, this solution was acidified with 1.0N HCl (12 ml) and partitioned between CH$_2$Cl$_2$ (50+25 ml) and brine (10 ml). The combined organic extracts were dried over MgSO$_4$, filtered and concentrated in vacuo. This residue was purified by column chromatography eluting with a 0-100% EtOAc/CH$_2$Cl$_2$ gradient to give N-(2-bromo-6-fluorophenyl)-methanesulfonamide. $^1$HNMR (400 MHz, CDCl$_3$) δ 7.41-7.47 (m, 1H), 7.16 (d, 1H, J=12.5 Hz), 7.14-7.17 (m, 1H), 6.22 (br s, 1H) and 3.27 (s, 3H) ppm.

To a solution of the above compound (142 mg, 0.530 mmol) in methanol (2 ml) was added 1.0N trimethylsilyl diazomethane in hexanes (1 ml, 1 mmol) and stirred for 3 hours. After this time, more trimethylsilyl diazomethane (1 ml, 1 mmol) was added and stirring continued for an additional 24 h. The resulting solution was concentrated in vacuo and the residue was purified by column chromatography eluting with a 25-100% CH2Cl2/hexanes gradient to give N-(2-bromo-6-fluorophenyl)-N-methylmethanesulfonamide. Low resolution mass spectrometry: (M+H$^+$) =282.0. $^1$H NMR (400 MHz, CDCl$_3$) δ 7.47 (d, 1H, J=8.1 Hz), 7.11-7.26 (m, 2H), 3.26 (s, 3H) and 3.12 (s, 3H)ppm.

A suspension of the above compound (74 mg, 0.262 mmol), tert-butyl(1R)-1-[2-fluoro-4-(4,4,5,5-tetramethyl-1,3,2-dioxaborolan-2-yl)phenyl]ethylcarbamate (92 mg, 0.262 mmol), tris(dibenzylideneacetone)dipalladium (24 mg, 0.026 mmol), cesium carbonate (85 mg, 0.262 mmol) and a solution of 1.0M tri-t-butylphosphine (63 ul, 0.063 mmol) in dioxane (0.5 ml) was heated to 85 C for 1 hour. After this time, the reaction mixture was diluted with EtOAc (5 ml) and aq NH$_4$Cl (1 ml) and filtered through a Gelman Acrodisc. The filtrates were partitioned and the aqueous layers back extracted with EtOAc (3 ml). The combined organic extracts were dried over MgSO$_4$, filtered and concentrated in vacuo. This residue was purified by column chromatography eluting with 0-20% EtOAc/CH$_2$Cl$_2$ to give tert-butyl {3,3'-difluoro-2'-[methyl(methylsulfonyl)amino]-1,1'-biphenyl-4-yl}methylcarbamate. Low resolution mass spectrometry: (M+H$^+$)=327.17 (−Boc). $^1$H NMR (400 MHz, CDCl$_3$) δ 7.34-7.44 (m, 2H), 7.12-7.24 (m, 4H), 4.95 (br s, 1H), 4.41 (br s, 2H), 3.08 (s, 3H), 2.87 (s, 3H) and 1.46 (s, 9H) ppm.

To a cooled solution of the above compound (68 mg, 0.159 mmol) in EtOAc (2 ml) was bubbled HCl gas for 2 minutes. This mixture was stirred at 0 C for 10 minutes and then allowed to warm to room temperature. The resulting mixture was concentrated in vacuo to give {3,3'-difluoro-2'-[methyl(methylsulfonyl)amino]-1,1'-biphenyl-4-yl}methanaminium chloride. Low resolution mass spectrometry: (M+H$^+$)=327.17. $^1$H NMR (400 MHz, CDCl$_3$) δ 8.7 (br s, 3H), 7.77 (t, 1H, J=7.8 Hz), 7.33-7.40 (m, 1H), 7.24-7.30 (m, 1H), 7.12-7.23 (m, 3H), 4.31 (br s, 2H), 3.05 (s, 3H) and 2.88 (s, 3H) ppm.

To a solution of the above compound (33 mg, 0.091 mmol), 1-[(pyrimidin-5-ylcarbonyl)amino]cyclopropanecarboxylic acid compound with chlorolithium (1:1) (23 mg, 0.091 mmol), EDC (17 mg, 0.091 mmol) and HOAT (12 mg, 0.091 mmol) was added triethylamine (13 ul, 0.091 mmol) and stirred at room temperature for 3 days. After this time, more EDC (17 mg, 0.091 mmol) and triethylamine (13 ul, 0.091 mmol) were added, and stirring continued for 30 minutes. This mixture was diluted with DMF (0.75 ml) and purified on the Gilson LC using a VYDAC C18 column and eluting with a 5-95% aq acetonitrile. The desired fractions were lyophilized to give N(1-{[({3,3'-difluoro-2'-[methyl(methylsulfonyl)amino]-1,1'-biphenyl-4-yl}methyl)amino] carbonyl}cyclopropyl)pyrimidine-5-carboxamide as a white solid. High resolution mass spectrometry: C$_{24}$H$_{24}$F$_2$N$_5$O$_4$S requires: 516.1512, found: 516.1508. $^1$H NMR (400 MHz, (CD$_3$)$_2$SO) δ 9.38 (s, 1H), 9.32 (s, 1H), 9.21 (s, 2H), 8.62 (t, 1H, J=5.9 Hz), 7.45-7.53 (m, 1H), 7.35-7.43 (m, 2H), 7.18-7.25 (m, 3H), 4.39 (d, 2H), J=5.9 Hz), 3.04 (s, 3H), 2.85 (s, 3H), 1.37-1.43 (m, 2H) and 1.05-1.09 (m, 2H) ppm.

EXAMPLE 18

N-(1-{[({3,3'-difluoro-2'-[(methylsulfonyl)amino]-1,1'-biphenyl-4-yl}methyl)amino]carbonyl}-cyclopropyl)pyrimidine-5-carboxamide

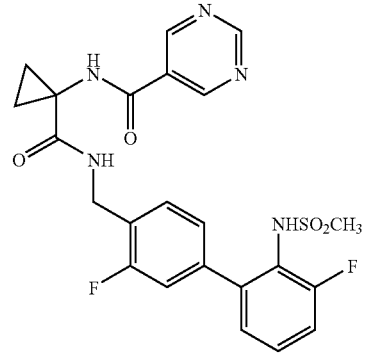

The title compound was prepared in an analogous manner as described in Example 17. High resolution mass spectrometry: C$_{23}$H$_{22}$F$_2$N$_5$O$_4$S requires: 502.1368, found: 502.1363. $^1$H NMR (400 MHz, (CD$_3$)$_2$SO) δ 9.37 (s, 1H), 9.31 (s, 1H), 9.25 (s, 1H), 9.21 (s, 2H), 8.62 (t, 1H, J=5.8 Hz), 7.21-7.48 (m, 6H), 4.38 (d, 2H, 5.8 Hz), 2.66 (s, 3H), 1.40 (q, 2H, 3.4 Hz) and 1.07 (q, 2H, 3.4 Hz) ppm.

EXAMPLE 19

N-{(1R)-1-[2'-({[4-(acetylamino)phenyl]sulfonyl}amino)-3,3'-difluorobiphenyl-4-yl]ethyl}-1-[(trifluoroacetyl)amino]cyclopropanecarboxamide

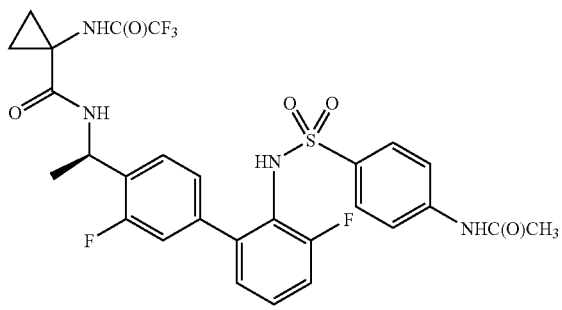

The title compound was prepared in an analogous manner as described in Example 17. MS (M+H$^+$ 626.3)

EXAMPLE 20

N-{1-[({[2'-(1,1-dioxido-1,2-thiazinan-2-yl)-3,3'-difluoro-1,1'-biphenyl-4-yl]methyl}amino)carbonyl]-cyclopropyl}pyrimidine-5-carboxamide

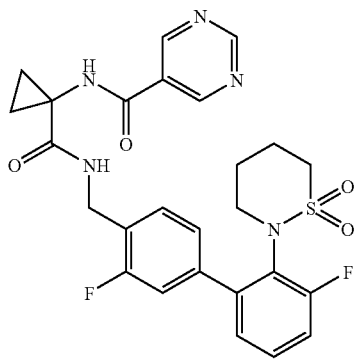

2-Bromo-1-fluoro-3-methoxybenzene (200 mg, 0.975 mmol), 1,2-thiazinane 1,1-dioxide (264 mg, 1.951 mmol), copper (62 mg, 0.975 mmol) and potassium carbonate (270 mg, 1.95 1 mmol) were combined and heated to 170 C for 5 hours. After this time, the mixture was suspended in methanol (15 ml) and vortexed for 18 hours. This mixture was filtered through Gelman Acrodisc and evaporated in vacuo. The resulting residue was partitioned between EtOAc (2×10 ml) and aq NH4Cl (5 ml). The combined organic extracts were dried over MgSO$_4$, filtered and concentrated in vacuo. This residue was purified by column chromatography eluting with a 0-10% EtOAc/CH$_2$Cl$_2$ to give 2-(2-fluoro-6-methoxyphenyl)-1,2-thiazinane 1,1-dioxide. Low resolution mass spectrometry: (M+H$^+$)=260.1. $^1$H NMR (400 MHz, CDCl$_3$) δ 7.21 (dt, 1H, J=8.1 and 4.3 Hz), 6.69-6.77 (m, 21), 3.88 (s, 3H), 3.75-8.74 (m, 1H), 3.65 (dq, 1H, J=4.6, 6.0 and 14 Hz), 3.24 (dd, 2H, J=5.6 and 7.4 Hz), 3.27 (quin, 2H, J=6.1 Hz) and 1.78-1.90 (m, 2H) ppm.

To a solution of the above compound (58 mg, 0.224 mmol) in CH$_2$Cl$_2$ (1 ml) cooled over dry ice/acetone bath was added boron tribromide (224 ul, 0.224 mmol) and stirred over night at room temperature. After this time, the mixture was treated with methanol (3×5 ml) and concentrated in vacuo to give 2-(1,1-dioxido-1,2-thiazinan-2-yl)-3-fluorophenol. Low resolution mass spectrometry: (M+H$_+$)=246.16. $^1$H NMR (400 MHz, CDCl$_3$) δ 7.19 (dd, 1H, J=8.4 and 15 Hz), 6.81 (d, 1H, J=8.4 Hz), 6.70 (t, 1H, 10 Hz), 3.82-3.90 (m, 1H), 3.60-3.68 (m, 1H), 3.34-3.43 (m, 1H), 3.26-3.34 (m, 1H), 2.34-2.43 (m, 2H), 1.94-2.08 (m, 1H) and 1.77-1.89 (m, 1H) ppm.

To a solution of the above compound (58 mg, 0.236 mmol) in CH$_2$Cl$_2$ (1 ml) cooled over dry ice/acetone bath was sequentially added triethylamine (82 ul, 0.473 mmol) and triflouromethanesulfonic anhydride (40 ul, 0.236 mmol) and stirred 10 minutes at −78 C and then warmed to room temperature. This solution was treated with aq sat NaHCO$_3$ and extracted with CH$_2$Cl$_2$ (2×2 ml). The combined extracts were concentrated in vacuo and purified by column chromatography eluting with a 25-100% CH$_2$Cl$_2$/hexanes gradient to give 2-(1,1-dioxido-1,2-thiazinan-2-yl)-3-fluorophenyl trifluoromethanesulfonate. Low resolution mass spectrometry: (M+H$^+$)=246.16. $^1$H NMR (400 MHz, CDCl$_3$) δ 7.41 (dt, 1H, J=5.5 and 8.4 Hz), 7.20-7.24 (m, 1H), 7.11 (d, 8.4 Hz), 4.08-4.18 (m, 1H), 4.49-3.57 (m, 1H), 3.35-3.44 (m, 1H), 3.23-3.32 (m, 1H), 2.30-2.46 (m, 2H), 1.98-2.13 (m, 1H) and 1.84-1.94 m, 1H)ppm.

The above compound (60 mg, 0.159 mmol), tert-butyl (1R)-1-[2-fluoro-4-(4,4,5,5-tetramethyl-1,3,2-dioxaborolan-2-yl)phenyl]ethylcarbamate (56 mg, 0.159 mmol), tetrakis(triphenylphosphine)palladium (18 mg, 0.016 mmol) and potassium phosphate (23 mg, 0.106 mmol) were combined in DME (0.5 ml) under Ar and heated to 70 C for 18 hours. After this time, the mixture was suspended in EtOAc (5 ml) and aq sat NH$_4$Cl (1 ml) and vortexed for 2 minutes. This suspension was filtered through Gelman Acrodisc. This filtrate was partitioned and the aqueous layer was extracted with EtOAc (3 ml). The combined organic extracts were dried over MgSO$_4$, filtered and concentrated in vacuo. This residue was purified by column chromatography eluting with a 0-5% EtOAc/CH$_2$Cl$_2$ gradient to give tert-butyl [2'-(1,1-dioxido-1,2-thiazinan-2-yl)-3,3'-difluoro-1,1'-biphenyl-4-yl]methylcarbamate. Low resolution mass spectrometry: (M+H$^+$)=353.13(–Boc). $^1$H NMR (400 MHz, CDCl$_3$) δ 7.41 (t, 1H, J=7.9 Hz), 7.34 (dt, 1H, J=5.4 and 8.2 Hz), 7.10=7.24 (m, 4H), 4.96 (br s, 1H), 4.42 (d, 2H, J=5.5 Hz), 3.47-3.56 (m, m1H, 3.32-3.41 (m, 1H), 3.18-3.28 (m, 1H), 2.86-2.95 (m, 1H), 2.14-2.34 (m, 2H), 1.65-1.80 (m, 1H), 1.46 (s, 9H) and 1.33-1.46 (m, 1H) ppm.

The above compound was used to prepare the title compound in an analogous manner to Example 18. High resolution mass spectrometry: C$_{26}$H$_{26}$F$_2$N$_5$O$_4$S requires: 542.1668, found: 542.1661. $^1$HNMR (400 MHz, (CD$_3$)$_2$SO) δ 9.37 (s, 1H), 9.32 (s, 1H), 9.21 (s, 2H), 8.62 (1H, 6.1 Hz), 7.33-7.49 (m, 3H), 7.16-7.24 (m, 3H), 4.38 (d, 2H, 6 Hz), 4.42-5.58 (m, 1H), 3.10-3.24 (m, 1H), 2.7-2.8 (m, 1H), 2.3-2.6 (m, 1), 1.96-2.16 (m, 2H), 1.54-1.66 (m, 1H), 1.41 (q, 2H, J=4 Hz), 1.26-1.39 (m, 1H), and 1.07 (q, 2H, J=4 Hz) ppm.

EXAMPLE 21

N-[(1R)-1-(3,3'-difluoro-2'-{[(trifluoromethyl)sulfonyl]methyl}-1,1'-biphenyl-4-yl)ethyl]-1-[(trifluoroacetyl)amino]cyclopropanecarboxamide

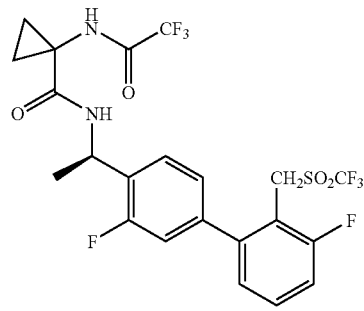

To a solution of 2-chloro-6-fluorobenzyl alcohol (0.50 g, 3.1 mmol) in ether (5 mL) at −10 C was added trifluoromethyl sulphonyl chloride, followed by a mixture of triethylamine (0.411 mL, 3.88 mmol) and trimethylphosphite (0.458 mLm, 3.88 mmol)) in ether (5 mL). The resulting mixture was stirred for 16 hours at room temperature and then partitioned between ether and water. The organic extract was washed with aq. HCl (0.5N), sat. aq. NaHCO$_3$ and dried (MgSO$_4$). The solvent was evaporated in vacuo to afford 2-chloro-6-fluorobenzyl trifluoromethanesulfinate as an oil. $^1$H NMR (400 MHz, CDCl$_3$)$_2$ δ 7.38 (1H, dt, J=6 and 8 Hz) 7.28 (1H, d, J=8 Hz), 7.08 (1H, dt, J=1, 8 Hz), 5.53 (1H, dd, J=1.8 and 11.1 Hz), 5.30 (1H, dd, J=0.7 and 11.1 Hz) ppm.

To a solution of the above compound (0.9 g, 3.25 mmol) in acetonitrile (12 mL) was added 2,6-lutidine (0.71 mL) and the mixture heated at reflux for 48 hours. The reaction was cooled to room temperature and the solvent evaporated in vacuo. The residue was dissolved in ether and washed with 0.5M aq. HCl, sat aq. NaHCO$_3$ and water. The organic extract was dried (MgSO$_4$) and evaporated in vacuo. The residue was purified by flash chromatography gradient elution with hexane to 50% diethyl ether in hexanes to afford 1-chloro-3-fluoro-2-{[(trifluoromethyl)sulfonyl]methyl}benzene as an oil. $^1$H NMR (400 MHz, CDCl$_3$)$_2$δ 7.40 (1H, dt, J=6 and 8 Hz) 7.34 (1H, d, J=8 Hz), 7.08 (1H, dt, J=1, 8 Hz), 4.80 (s, 2H) ppm.

To a solution of the above compound (91 mg, 0.34 mmol) in dioxane (0.5 mL) was added tri t-butyl phospine (0.025 mL of a 1.65M solution in dioxane, 0.04 mmol). To this solution was added Pd$_2$(dba)$_3$ (15.7 mg, 0.0017 mmol) Cs$_2$CO$_3$ (134 mg, 0.41 mmol) followed by tert-butyl(1R)-1-[2-fluoro-4-(4,4,5,5-tetramethyl-1,3,2-dioxaborolan-2-yl)phenyl]ethylcarbamate (130 mg, 0.36 mmol), the resulting suspension was heated at 80 C for 24 hours. The reaction was cooled to room temperature diluted with DMF (4 mL) and filtered. The resulting filtrate was purified by reverse phase HPLC C-18 gradient elution with 5:95% to 95:5% acetonitrile:water containing 0.1% TFA to tert-butyl(1R)-1-(3,3'-difluoro-2'-{[(trifluoromethyl)sulfonyl]methyl}-1,1'-biphenyl-4-yl)ethylcarbamate after lyophilization. Low resolution mass spectrum M$^+$-t-BocNH=363.

A solution of the above compound (33 mg, 0.068 mmol) in EtOAc (5 mL) was treated with HCl gas at 0 C After 5 minutes the solvent was evaporated in vacuo to afford (1R)-1-(3,3'-difluoro-2'-{[(trifluoromethyl)sulfonyl]methyl}-1,1'-biphenyl-4-yl)ethanaminium chloride. Low resolution mass spectrum MH$^+$=380.

To a solution of the above compound (26 mg, 0.062 mmol), 1-[(trifluoroacetyl)amino]-cyclopropanecarboxylic acid (1.5 mg, 0.069 mmol), HOAT (9.4 mg, 0.069 mmol) in DMP (1 mL) was added EDC (13.2 mg, 0.069 mmol) and triethylamine (0.026 mL, 0.187 mmol). The reaction was stirred at room temperature for 16 hours, diluted with DMF (1 mL) and purified by reverse phase HPLC C-18 gradient elution with 5:95% to 95:5% acetonitrile:water containing 0.1% TFA to afford the title compound as a solid after lyophilization. High resolution mass spectrum C$_{22}$H$_{18}$F$_8$N$_2$O$_4$S MH+ found 559.0951 requires 559.0933. $^1$H NMR (400 MHz, CDCl$_3$)$_2$δ 7.48 (1H, dt, J=6 and 8 Hz) 7.33 (1H, d, J=8 Hz), 7.22 (1H, dt, J=1, 8 Hz), 7.14 (1H, d, J=7.6 Hz), 7.12-7.05 (2H, m), 7.07 m(1H, s), 6.60 (1H, d, J=8 Hz), 5.26 (1H, qn, J=7 Hz), 4.61 (s, 2H), 1.64 (2H, m), 1.15 (2H, m) ppm.

EXAMPLE 22

N-[(1R)-1-(3,3'-difluoro-2'-{[(trifluoromethyl)sulfonyl]amino}-1,1'-biphenyl-4-yl)ethyl]-1-[(trifluoroacetyl)amino]cyclopropanecarboxamide

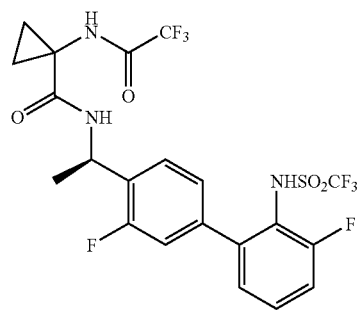

N-{(1R)-1-[2-fluoro-4-(4,4,5,5-tetramethyl-1,3,2-dioxaborolan-2-yl)phenyl]ethyl}-1-[(trifluoroacetyl)amino]cyclopropanecarboxamide (1.50 g, 3.377 mmol), 2-bromo-6-flouroaniline (401 ul, 3.545 mmol), tris(dibenzylideneacetone)dipalladium (309 mg, 0.338 mmol), cesium carbonate (1.10 g, 3.377 mmol) and 1.65M tri-t-butylphosphine in dioxane (491 ul, 0.810 mmol) were suspended in dioxane (15 ml), degassed with Argon purge and heated to 90 C for 15 minutes. After this time, the mixture was filtered through a Gelman Acrodisc and the filter was washed with EtOAc (10 ml) and methanol (20 ml). The combined filtrates were concentrated in vacuo and the residue purified by column chromatography eluting with a 0-100% EtAOc/CH$_2$Cl$_2$ gradient to give N-[(1R)-1-(2'-amino-3,3'-difluoro-1,1'-biphenyl-4-yl)ethyl]-1-[(trifluoroacetyl)amino]cyclopropanecarboxamide. Low resolution mass spectrometry: (M+H$^+$)=428.2. $^1$H NMR (400 MHz, (CD$_3$)$_2$SO) δ 9.79 (s, 1H), 8.28 (d, 1H, J=7.6 Hz), 7.48 (t, 1H, J=8.2 Hz), 7.19-7.26 (m, 2H), 7.02-7.09 (m, 1H), 6.89 (d, 1H, J=7.6 Hz), 6.61-6.68 (m, 1H), 5.22-5.29 (m, 1H), 1.45-1.57 (m, 2H), 1.42 (d, 3H, J=7.1 Hz) and 0.93-1.08 (m, 2H) ppm.

A solution of the above compound (50 mg, 0.117 mmol) in CH$_2$Cl$_2$ (0.5 ml) was cooled over a dry ice/acetone bath and then treated sequentially with diisopropylethylamine (41 ul, 0.234 mmol) and trifluoromethanesulfonic anhydride (20 ul, 0.117 mmol) and then warmed to room temperature and stirred for 4 hours. The resulting mixture was diluted with methanol, filtered and purified by reverse phase chromatography using a 5-95% aq ACN gradient. The desired fractions were combined and lyophilized to give the title compound as a white solid. High resolution mass spectrometry: C$_{21}$H$_{17}$F$_8$N$_3$O$_4$S requires: 560.0885, found: 560.0884. $^1$H NMR (400 MHz, CD3CN) δ 8.10 (s, 1H), 7.52 (dt, 1H, J=5.7 and 8.1 Hz), 7.41 (t, 1H, J=8.1 Hz), 7.26-7.33 (m, 2H), 7.21 (dd, 1H, J=1.7 and 8.1 Hz), 7.17 (dd, 1H, J=1.7 and 11.5 Hz), 7.14-7.24 (m, 1H), 5.26 (quin, 1H, J=7.3 Hz), 1.46 (d, 3H, J=6.9 Hz), 1.34-1.45 (m, 2H), 1.08-1.15 (m, 1H) and 1.01-1.07 (m, 1H) ppm.

EXAMPLE 23

N-(1-{[((1R)-1-{3,3'-difluoro-2'-[(methylsulfonyl)amino]-1,1'-biphenyl-4-yl}ethyl)amino]carbonyl}-cyclopropyl)pyrimidine-5-carboxamide

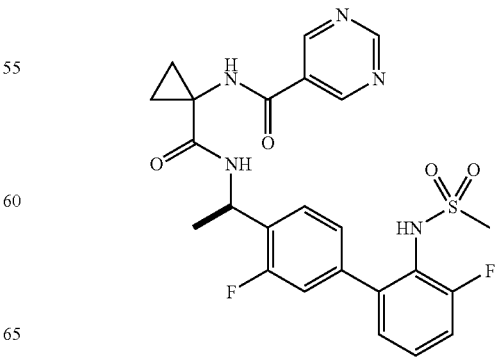

To a solution of N-[(1R)-1-(2'-amino-3,3'-difluoro-1,1'-biphenyl-4-yl)ethyl]-1-[(trifluoroacetyl)amino]cyclopropanecarboxamide (174 mg 0.407 mmol) in methanol (2 ml) was added 1.0N NaOH (2 ml, 2 mmol) and stirred at room temperature 4 days. This mixture was concentrated under vacuum to a 2 ml volume and extracted with methylene chloride (2×10 ml). The combined extracts were washed with water (1 ml), dried over MgSO4, filtered and the solvent removed in vacuo to give 1-amino-N-[(1R)-1-(2'-amino-3,3'-difluoro-1,1'-biphenyl-4-yl)ethyl]cyclopropanecarboxamide. Low resolution mass spectrometry: (M+H$^+$) =332.3.

To a solution of the above compound (123 mg, 0.371 mmol) in DMF (2 mmol) was added 5-pyrimidinecarboxylic acid (46 mg, 0.371 mmol), HOAT (51 mg, 0.371 mmol), triethylamine (38 mg, 0.371 mmol) and EDC (71 mg, 0.371 mmol) and the mixture stirred for 18 h. This mixture was purified directly on Gilson LC using Waters PrepPak and eluting with an 5-95% aq ACN gradient over 20 min. The desired fractions were lyophilized and the resulting amorphous solid was dissolved in CH$_2$Cl2, washed with aq. Na2CO3, dried over MgSO4, filtered and the solvent removed in vacuo to give N-[1-({[(1R)-1-(2'-amino-3,3'-difluoro-1,1'-biphenyl-4-yl)ethyl]amino}carbonyl)cyclopropyl]pyrimidine-5-carboxamide the title compound. Low resolution mass spectrometry: (M+H+)=438.3

To a solution of the above compound (27 mg, 0.062 mmol) in pyridine (500 ul) was added methanesulfonic acid anhydride (22 mg, 0.123 mmol) and heated to 70° C. for 2 h. To this mixture was added additional methanesulfonic anhydride (33 mg, 0.186 mmol) and heated to 70° C. for 18 h. This mixture was concentrated under vacuum and the resulting oil was purified on the Gilson LC system using a Jupiter column (10u, C18, 300 Å) and eluting with 5-95% aq ACN gradient. Both the title compound and the bis mesylate by product were isolated by lyophilizing the corresponding fractions. The bis mesylate was dissolved in methanol and treated with 1.0N NaOH and repurified as above to give additional title compound as an amorphous solid. Low resolution mass spectrometry: (M+H+)=516.3.

$^1$H NMR (400 MHz, (CD3OD) δ 9.33 (s, 1H), 9.29 (s, 1H), 9.24 (s, 2H), 8.33 (d, J=8.0 Hz, 1H), 7.47 (t, J=8 Hz, 1H), 7.43-7.36 (m, 1H), 7.28-7.16 (m, 4H), 5.34 (quintet, J=7.1 Hz, 1H), 2.73 (s, 3H), 1.59-1.50 (m, 2H), 1.50 (d, J=7.1 Hz, 2H) and 1.24-1.11 (m, 2H) ppm.

EXAMPLE 23A

N-(1-{[((1R)-1-{3,3'-difluoro-2'-[([35S]methylsulfonyl)amino]-1,1'-biphenyl-4-yl}ethyl)amino]-carbonyl}cyclopropyl)pyrimidine-5-carboxamide N-(1-{[((1R)-1-{2'-amino-3,3'-difluoro-1,1'-biphenyl-4-yl}ethyl)amino]carbonyl}cyclopropyl)pyrimidine-5-carboxamide (9 mg, 0.02 mmol) was dissolved in pyridine (10 uL). [35S]Methanesulfonyl chloride (40 mCi) in methylene chloride was distilled at atmospheric pressure to a volume of approximately 50 uL and added to the amine solution. The reaction mixture was aged at room temperature for 2 hours, diluted with ethyl acetate (10 mL), and extracted with 10% aqueous sodium bicarbonate solution (2×5 mL). The organic phase was concentrated and the residue purified by preparative HPLC (Zorbax RX C8, 25/75 A/B to 30/70 A/B, A=CH3CN, B=0.1% TFA). Following isolation, the tracer was further purified by preparative HPLC (Luna C8, 25/75 A/B to 32.5/67.5 A/B, A=CH3CN, B=0.1% TFA) to afford 75 uCi of the title compound. The identity of the tracer was confirmed by co-elution on HPLC (Zorbax SB-phenyl 55/45 MeOH/0.1% HClO4) with authentic standard.

EXAMPLE 24

N-[(1R)-1-(2-fluoro-4-{1-[(trifluoromethyl)sulfonyl]-1,2,3,4-tetrahydroquinolin-8-yl}phenyl)ethyl]-1-[(trifluoroacetyl)amino]cyclopropanecarboxamide

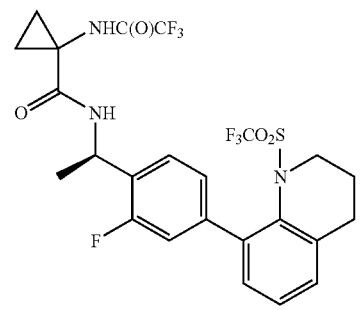

N-{(1R)-1-[2-Fluoro-4-(4,4,5,5-tetramethyl-1,3,2-dioxaborolan-2-yl)phenyl]ethyl}-1-[(trifluoroacetyl)amino]cyclopropanecarboxamide (250 mg, 0.563 mmol), 8-bromoquinoline (117 mg, 0.563 mmol), cesium carbonate (367 mg, 1.13 mmol), and bis(tri-t-butylphosphine) palladium(0) (10 mg, 0.03 mmol) were stirred in 1 mL of anhydrous dioxane overnight at 90° C. in a sealed tube. The reaction mixture was cooled to room temperature and diluted w/EtOAc. The organic layer was separated, washed with water and brine, dried over sodium sulfate, filtered, and concentrated under reduced pressure. The crude material was purified by silica gel chromatography eluting with 10% to 95% EtOAc/hexanes to provide (N-[(1R)-1-(2-fluoro-4-quinolin-8-yl)phenyl)ethyl]-1-[(trifluoroacetyl)amino]cyclopropanecarboxamide. ES MS, M+H+ found: 475. Proton NMR (400 MHz, CDCl$_3$) δ 1.2 (m, J=2.4 Hz, 2H), 1.58 (d, J=6.8 Hz, 3H), 1.7 (m, J=2.9 Hz, 2H), 3.86 (s, 3H), 5.33 (q, J=7.2 Hz, 1H), 6.64 (d, J=8.8 Hz, 1H), 6.84 (s, 1H), 7.08 to 7.19 (m, 3H), 7.34 (m, 3H), 7.47 (m, J=4.5 Hz, 1H), 7.81 (m, J=5 Hz, 1H), 7.9 (d, J=9 Hz, 1H).

The above compound (40 mg, 0.09 mmol) was dissolved in 1 ml of 1:1 EtOH/EtOAc, and the solution was purged with N$_2$ for 10 minutes. 10% Pd-C catalyst (2 mg, 0.016 mmol) was added and the mixture purged for an additional 10 minutes. A balloon of hydrogen was fitted and the reaction stirred for 16 hrs. The mixture was purged with nitrogen, filtered through celite, washing with 2.0 M NH3 in MeOH, and the filtrate concentrated under reduced pressure. The crude material was purified by silica gel chromatography eluting with 10% to 95% EtOAc/hexanes to provide N-{(1R)-1-[2-fluoro-4-(1,2,3,4-tetrahydroquinolin-8-yl)phenyl]ethyl}-1-[(trifluoroacetyl)amino]cyclopropanecarboxamide. ES MS, M+H+ found: 450.

The above compound (40 mg) was dissolved in 1 ml of methylene chloride, and triethylamine (0.014 mL, 1.1 equiv) was added. The solution was cooled to −78° C. and triflic anhydride (0.018 mL, 1.3 equiv) was added slowly. After 30 minutes, another 1.3 equivalents of triflic anhydride was added. After another 30 minutes, the solution was warmed to room temperature and the reaction quenched with saturated sodium bicarbonate. The organic layer was separated, dried over sodium sulfate, concentrated under reduced pressure, and subjected to silica gel chromatography eluting with 5% to 75% EtOAc/hex. Further separation by preparative TLC on a 1 mm plate using 10% Et2O/DCM as the eluent provided the title compound. ES MS, M+H$^+$ found: 582. Proton NMR (400 MHz, CDCl$_3$) δ 1.1 (m, 2H), 1.52 (d, J=7.1 Hz, 3H), 1.65 (m, 2H), 1.9 (m, 1H), 2.5 (m, 1H), 2.8

(m, 2H), 3.5 (m, 1H), 4.2 (m, 1H), 5.25 (q, J=7 Hz, 1H), 6.6 (d, J=8.2 Hz, 1H), 6.8 (d, J=8.2 Hz, 1H), 7.03 to 7.09 (m, 2H), 7.31 to 7.35 (m, 2H).

What is claimed is:

1. A compound of formula I and pharmaceutically acceptable salts thereof:

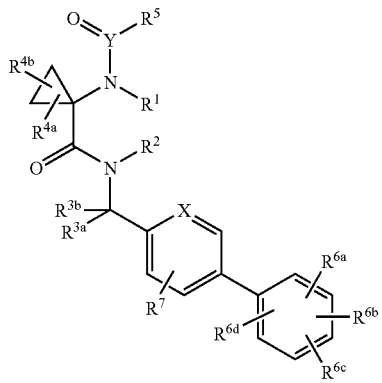

I wherein
- $R^1$ and $R^2$ are independently selected from hydrogen and $C_{1-4}$ alkyl;
- $R^{3a}$ and $R^{3b}$ are independently selected from hydrogen and $C_{1-4}$ alkyl optionally substituted with 1 to 5 halogen atoms;
- $R^{4a}$ and $R^{4b}$ are independently selected form hydrogen, halogen, and $C_{1-4}$ alkyl optionally substituted with 1 to 4 groups selected from halogen, $OR^a$, $OC(O)R^a$, $S(O)_k R^d$, $OS(O)_2 R^d$, and $NR^1R^2$, or
- $R^{4a}$ and $R^{4b}$ together with the carbon atom to which they are both attached form an exo-cyclic methylene optionally substituted with 1 to 2 groups selected from $C_{1-4}$ alkyl optionally substituted with 1-5 halogens and $C_{1-4}$ alkyloxy;
- $R^5$ is selected from (1) $C_{1-6}$ alkyl optionally substituted with 1 to 5 groups independently selected from halogen, nitro, cyano, $OR^a$, $SR^a$, $COR^a$, $SO_2R^d$, $CO_2R^a$, $OC(O)R^a$, $NR^bR^c$, $NR^bC(O)R^a$, $NR^bC(O)_2R^a$, $C(O)NR^bR^c$, $C_{3-8}$ cycloalkyl, (2) $C_{3-8}$ cycloalkyl optionally substituted with 1 to 5 groups independently selected from halogen, nitro, cyano and phenyl, (3) $C_{3-6}$ alkynyl, (4) $C_{2-6}$ alkenyl optionally substituted with hydroxyethyl, (5) $(CH_2)_k$-aryl optionally substituted with 1 to 3 groups independently selected from halogen, nitro, cyano, $OR^a$, $SR^a$, $C(O)_2R^a$, $C_{1-4}$ alkyl and $C_{1-3}$ haloalkyl; (6) $(CH_2)_k$-heterocycle optionally substituted with 1 to 3 groups independently selected from halogen, nitro, cyano, $OR^a$, $SR^a$, $C_{1-4}$ alkyl and $C_{1-3}$ haloalkyl wherein said heterocycle is selected from (a) a 5-membered heteroaromatic ring having a ring heteroatom selected from N, O and S, and optionally having up to 3 additional ring nitrogen atoms wherein said ring is optionally benzo-fused; (b) a 6-membered heteroaromatic ring containing from 1 to 3 ring nitrogen atoms and N-oxides thereof, wherein said ring is optionally benzo-fused; and (c) a 5- or 6-membered non-aromatic heterocyclic ring selected from tetrahydrofuranyl, 5-oxotetrahydrofuranyl, 2-oxo-2H-pyranyl, 6-oxo-1,6-dihydropyridazinyl, (7) $C(O)_2R^a$, and (8) $C(O)NR^bR^c$;
- $R^{6a}$ is $OSO_2R^8$;
- $R^{6b}$, $R^{6c}$, and $R^{6d}$ are independently selected from (1) hydrogen, (2) halogen, (3) $OSO_2R^8$, (4) $C_{1-4}$ alkyl optionally substituted with 1 to 5 halogen atoms, (5) cyano, (6) nitro, (7) $OR^a$, and (8) $CO_2R^a$, or
- when attached to adjacent carbon atoms $R^{6c}$ and $R^{6d}$ together with the carbon atoms to which they are attached form a 5- to 8-membered saturated or unsaturated ring;
- $R^7$ is selected from (1) hydrogen, (2) halogen, (3) cyano, (4) nitro, (5) $OR^a$, (6) $CO_2R^a$, (7) $C(O)NR^bR^c$, and (8) $C_{1-4}$ alkyl optionally substituted with 1 to 5 halogen atoms,
- $R^8$ is selected from (1) $C_{1-4}$ alkyl optionally substituted with 1 to 5 halogen atoms, (2) $(CH_2)_k$-aryl optionally substituted with 1 to 3 groups independently selected from halogen, nitro, cyano, $NR^aC(O)R^a$, $OR^a$, $SR^a$, $CO_2R^a$, $C_{1-4}$ alkyl, $C_{1-3}$ haloalkyl and $NR^bR^c$, (3) $NR^bR^c$, and (4) hydrogen;
- $R^a$, $R^b$ and $R^c$ are independently selected from (1) hydrogen, (2) $C_{1-4}$ alkyl optionally substituted with 1 to 5 halogen atoms, (3) phenyl optionally substituted with 1 to 3 groups selected from halogen, cyano, nitro, OH, $C_{1-4}$ alkyloxy, $C_{3-6}$ cycloalkyl and $C_{1-4}$ alkyl optionally substituted with 1 to 5 halogen atoms, and (4) $C_{3-6}$ cycloalkyl, or
- $R^b$ and $R^c$ together with the nitrogen atom to which they are attached form a 4-, 5-, or 6-membered ring optionally containing an additional heteroatom selected from N, O, and S; or
- $R^b$ and $R^c$ together with the nitrogen atom to which they are attached form a cyclic imide;
- $R^d$ is selected from (1) $C_{1-4}$ alkyl optionally substituted with 1 to 5 halogen atoms, (2) $C_{1-4}$ alkyloxy, (3) phenyl optionally substituted with 1 to 3 groups selected from halogen, cyano, nitro, OH, $C_{1-4}$ alkyloxy, $C_{3-6}$ cycloalkyl and $C_{1-4}$ alkyl optionally substituted with 1 to 5 halogen atoms, and (4) hydrogen;
- X is selected from CH and N;
- Y is selected from C and S=O; and
- k is selected from 0, 1, and 2.

2. A compound of claim 1 wherein $R^5$ is selected from pyrimidinyl and $C_{1-6}$ alkyl optionally substituted with 1 to 5 groups independently selected from halogen.

3. A compound of claim 1 wherein Y is C.

4. A compound of claim 1 $R^8$ is selected from 2,2,2,-trifluoromethyl, methyl, ethyl, propyl, isopropyl, phenyl, benzyl, and dimethylamino.

5. A compound of claim 1 wherein $R^{6b}$ is selected from hydrogen, fluorine, and chlorine.

6. A compound of claim 1 having the formula I(2):

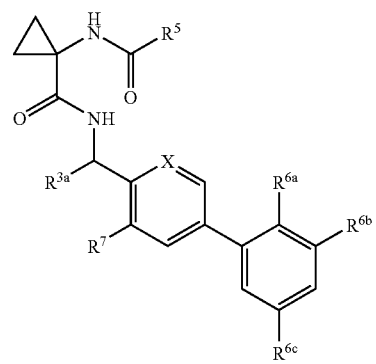

I(2)

wherein X is N or CH, $R^{3a}$ is H or $C_{1-4}$ alkyl, $R^7$ is hydrogen or halogen, and $R^5$, $R^{6a}$, $R^{6b}$ and $R^{6c}$ have the same definitions as provided in claim 1.

7. A compound of claim 6 wherein $R^{6a}$ is $OSO_2R^8$; $R^8$ is selected from methyl, trifluoromethyl, ethyl, propyl, isopropyl, benzyl, dimethylamino, 2,2,2-trifluoroethyl, and phenyl; $R^{6b}$ is hydrogen or halogen, and $R^{6c}$ is hydrogen or halogen.

8. A compound of claim 6 wherein R5 is pyrimidinyl or $C_{1-4}$ alkyl optionally substituted with 1 to 5 groups independently selected from halogen.

9. A compound selected from
3,3'-difluoro-4'-{[({1-[(pyrimidin-5-ylcarbonyl)amino]cyclopropyl}carbonyl)amino]methyl}-1,1'-biphenyl-2-yl trifluoromethanesulfonate,
3,3'-difluoro-4'-{(1R)-1-[({1-[(trifluoroacetyl)amino]cyclopropyl}carbonyl)amino]ethyl}-1,1'-biphenyl-2-yl trifluoromethanesulfonate,
3,3'-difluoro-4'-((1R)-1-{[(1-{[(trifluoromethyl)sulfonyl]amino}cyclopropyl)carbonyl]amino}-ethyl)-1,1'-biphenyl-2-yl trifluoromethanesulfonate,
1-({[(1R)-1-(3,3'-difluoro-2'-{[(trifluoromethyl)sulfonyl]oxy}-1,1'-biphenyl-4-yl)ethyl]amino}-carbonyl)cyclopropanaminium trifluoroacetate,
3,3'-difluoro-4'-{(1R)-1-[({1-[(trifluoroacetyl)amino]cyclopropyl}carbonyl)amino]ethyl}-1,1'-biphenyl-2-yl methanesulfonate,
5-chloro-3,3'-difluoro-4'-{(1R)-1-[({1-[(trifluoroacetyl)amino]cyclopropyl}carbonyl)amino]-ethyl}-1,1'-biphenyl-2-yl trifluoromethanesulfonate,
3,3'-difluoro-4'-{(1R)-1-[({1-[(trifluoroacetyl)amino]cyclopropyl}carbonyl)amino]ethyl}-1,1'-biphenyl-2-yl methanesulfonate,
3,3'-difluoro-4'-{(1R)-1-[({1-[(trifluoroacetyl)amino]cyclopropyl}carbonyl)amino]ethyl}-1,1'-biphenyl-2-yl propane-1-sulfonate
3,3'-difluoro-4'-{(1R)-1-[({1-[(trifluoroacetyl)amino]cyclopropyl}carbonyl)amino]ethyl}-1,1'-biphenyl-2-yl propane-2-sulfonate,
3,3'-difluoro-4'-{(1R)-1-[({1-[(trifluoroacetyl)amino]cyclopropyl}carbonyl)amino]ethyl}-1,1'-biphenyl-2-yl benzenesulfonate,
3,3'-difluoro-4'-{(1R)-1-[({1-[(trifluoroacetyl)amino]cyclopropyl}carbonyl)amino]ethyl}-1,1'-biphenyl-2-yl phenylmethanesulfonate
3,3'-difluoro-4'-{(1R)-1-[({1-[(trifluoroacetyl)amino]cyclopropyl}carbonyl)amino]ethyl}-1,1'-biphenyl-2-yl dimethylsulfamate,
3,3'-difluoro-4'-{(1R)-1-[({1-[(trifluoroacetyl)amino]cyclopropyl}carbonyl)amino]ethyl}-1,1'-biphenyl-2-yl 2,2,2-trifluoroethanesulfonate,
3-chloro-3'-fluoro-4'-{(1R)-1-[({1-[(trifluoroacetyl)amino]cyclopropyl}carbonyl)amino]ethyl}-1,1'-biphenyl-2-yl trifluoromethanesulfonate,
3'-fluoro-4'-{(1R)-1-[({1-[(trifluoroacetyl)amino]cyclopropyl}carbonyl)amino]ethyl}-2-{[(trifluoromethyl)sulfonyl]oxy}-1,1'-biphenyl-3-yl trifluoromethanesulfonate,
N-(1-{[(((1R)-1-{3,3'-difluoro-2'-[methyl(methylsulfonyl)amino]-1,1'-biphenyl-4-yl}ethyl)amino]-carbonyl)cyclopropyl}pyrimidine-5-carboxamide,
N-(1-{[({3,3'-difluoro-2'-[(methylsulfonyl)amino]-1,1'-biphenyl-4-yl}methyl)amino]carbonyl}-cyclopropyl)pyrimidine-5-carboxamide,
N-{1-[({[2'-(1,1-dioxido-1,2-thiazinan-2-yl)-3,3'-difluoro-1,1'-biphenyl-4-yl]methyl}amino)carbonyl]-cyclopropyl}pyrimidine-5-carboxamide,
N-[(1R)-1-(3,3'-difluoro-2'-{[(trifluoromethyl)sulfonyl]methyl}-1,1'-biphenyl-4-yl)ethyl]-1-[(trifluoroacetyl)amino]cyclopropanecarboxamide,
N-[(1R)-1-(3,3'-difluoro-2'-{[(trifluoromethyl)sulfonyl]amino}-1,1'-biphenyl-4-yl)ethyl]-1-[(trifluoroacetyl)amino]cyclopropanecarboxamide, and
N-(1-{[(((1R)-1-{3,3'-difluoro-2'-[(methylsulfonyl)amino]-1,1'-biphenyl-4-yl}ethyl)amino]-carbonyl}-cyclopropyl)pyrimidine-5-carboxamide.

10. A pharmaceutical composition comprising a therapeutically effective amount of a compound of claim 1 and a pharmaceutically acceptable carrier.

11. The compound N-[(1R)-1-(2-fluoro-4-{1-[(trifluoromethyl)sulfonyl]-1,2,3,4-tetrahydroquinolin-8-yl}phenyl)ethyl]-1-[(trifluoroacetyl)amino]cyclopropanecarboxamide.

* * * * *